US007977015B2

(12) United States Patent
Suzuki et al.

(10) Patent No.: US 7,977,015 B2
(45) Date of Patent: Jul. 12, 2011

(54) POLYMERIZABLE COMPOUND, OPTICAL RECORDING COMPOSITION, HOLOGRAPHIC RECORDING MEDIUM AND METHOD OF RECORDING INFORMATION

(75) Inventors: Hiroyuki Suzuki, Kanagawa (JP); Satoru Yamada, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 613 days.

(21) Appl. No.: 12/028,499

(22) Filed: Feb. 8, 2008

(65) Prior Publication Data

US 2008/0193858 A1 Aug. 14, 2008

(30) Foreign Application Priority Data

Feb. 8, 2007 (JP) ................................. 2007/029591

(51) Int. Cl.
*G03F 7/004* (2006.01)
*C07C 69/76* (2006.01)

(52) U.S. Cl. .......... 430/1; 430/2; 430/280.1; 430/281.1; 359/3; 522/117; 522/34; 522/35; 560/56

(58) Field of Classification Search ........................ None
See application file for complete search history.

(56) References Cited

U.S. PATENT DOCUMENTS 3,607,693 A * 9/1971 Heine et al. ...................... 522/44
4,086,299 A * 4/1978 Jackson et al. ................ 522/117
4,148,987 A * 4/1979 Winey ........................... 526/316

(Continued)

FOREIGN PATENT DOCUMENTS

JP 11-311936 A 11/1999

(Continued)

OTHER PUBLICATIONS

Woo et al. "photopolymerization of methyl methacrylate initiated by benzoin derivatives", Bull. Korean Chem. Soc., vol. 16(67) pp. 667-670 (1995).*

(Continued)

*Primary Examiner* — Martin J Angebranndt

(74) *Attorney, Agent, or Firm* — Birch, Stewart, Kolasch & Birch, LLP

(57) ABSTRACT

The present invention provides a polymerizable compound denoted by general formula (1).

General formula (1)

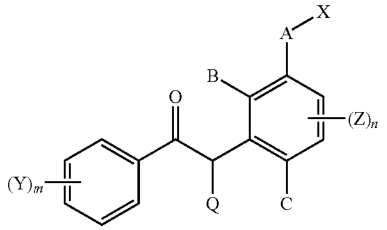

In general formula (1), A denotes an oxygen atom, sulfur atom, or NR, R denotes a hydrogen atom, alkyl group, aryl group, or heterocyclic group, X denotes a hydrogen atom, polymerizable group, optionally polymerizable group-substituted alkyl group or the like, B and C each independently denote a hydrogen atom, halogen atom, polymerizable group, optionally polymerizable group-substituted alkyl group or the like, wherein at least one from among B and C denotes a hydrogen atom and at least one from among X, Y, and Z comprises a polymerizable group, m denotes an integer ranging from 0 to 5, n denotes an integer ranging from 0 to 2, and Q denotes an elimination group.

7 Claims, 4 Drawing Sheets

U.S. PATENT DOCUMENTS

| | | | | |
|---|---|---|---|---|
| 4,672,079 | A * | 6/1987 | Li Bassi et al. | 522/35 |
| 5,506,279 | A * | 4/1996 | Babu et al. | 522/34 |
| 6,124,076 | A | 9/2000 | Dhar et al. | |
| 7,141,354 | B2 * | 11/2006 | Sakayori | 430/281.1 |
| 2002/0004172 | A1 * | 1/2002 | Maeda et al. | 430/1 |
| 2002/0114027 | A1 | 8/2002 | Horimai | |

FOREIGN PATENT DOCUMENTS

| | | | |
|---|---|---|---|
| JP | 2000-086914 | B2 | 3/2000 |
| JP | 2004-507513 | A | 3/2004 |
| JP | 2005-502918 | A | 1/2005 |
| WO | WO-02/19040 | A2 | 3/2002 |
| WO | WO-03/023519 | A1 | 3/2003 |

OTHER PUBLICATIONS

Angiolini et al."Polymeric photoinitiators having benzoin methyl ether moieties .."Polymer vol. 40 pp. 7197-7207 (1999).*

Corrales et al., "Free radical macrophotoinitiator"an overview . . . )J. Photochem. Photobiol. A:Chem., vol. 159 pp. 103-114 (2003).*

Crivello et al. "Photoinitiators for free radical cationic and anionic photopolymerization", vol. III, second Ed, pp. 208-224 (1998).*

Journal of the Japanese Society of Printing Science and Technology, 2004, vol. 41, p. 25-31.

Journal of the American Chemical Society, 1971, vol. 93, p. 7222-7228.

Tetrahedron, 2004, vol. 60, p. 3803-3811.

* cited by examiner

POLYMERIZABLE COMPOUND, OPTICAL RECORDING COMPOSITION, HOLOGRAPHIC RECORDING MEDIUM AND METHOD OF RECORDING INFORMATION

CROSS-REFERENCE TO RELATED APPLICATIONS

This application claims the benefit of priority under 35 USC 119 to Japanese Patent Application No. 2007-029591 filed on Feb. 8, 2007, which is expressly incorporated herein by reference in its entirety.

BACKGROUND OF THE INVENTION

1. Field of the Invention

The present invention relates to a polymerizable compound suited to the manufacturing of a holographic recording medium, especially a volume holographic recording medium. The present invention further relates to an optical recording composition comprising the above polymerizable compound, a holographic recording medium formed with the above optical recording composition, and a method of recording information on the above medium.

2. Discussion of the Background

Holographic optical recording media based on the principle of the holograph have been developed. Recording of information on holographic optical recording media is carried out by superposing an informing light containing image information and a reference light in a recording layer comprised of a photosensitive composition to write an interference fringe thus formed in the recording layer. During the reproduction of information, a reference light is directed at a prescribed angle into the recording layer in which the information has been recorded, causing optical diffraction of the reference light by the interference fringe which has been formed, reproducing the informing light.

In recent years, volume holography, and, more particularly, digital volume holography, have been developed to practical levels for ultrahigh-density optical recording and have been garnering attention. Volume holography is a method of writing interference fringes three-dimensionally by also actively utilizing the direction of thickness of an optical recording medium. It is advantageous in that increasing the thickness permits greater diffraction efficiency and multiplexed recording increases the recording capacity. Digital volume holography is a computer-oriented holographic recording method in which the image data being recorded are limited to a binary digital pattern while employing a recording medium and recording system similar to those of volume holography. In digital volume holography, for example, image information such as an analog drawing is first digitized and then expanded into two-dimensional digital pattern information, which is recorded as image information. During reproduction, the digital pattern information is read and decoded to restore the original image information, which is displayed. Thus, even when the signal-to-noise (S/N) ratio deteriorates somewhat during reproduction, by conducting differential detection or conducting error correction by encoding the two-dimensional data, it is possible to reproduce the original data in an extremely faithful manner (see Japanese Unexamined Patent Publication (KOKAI) Heisei No. 11-311936 or English language family member US 2002/0114027 A1, which are expressly incorporated herein by reference in their entirety).

For example, Published Japanese Translation of a PCT International Application (TOKUHYO) No. 2005-502918 or English language family member WO 03/023519, which are expressly incorporated herein by reference in their entirety, disclose the use of a urethane matrix and a phenyl acrylate derivative in a holographic optical recording medium of the photopolymer type. However, with common photopolymers, there is a major problem in that the polymerization of monomers is accompanied by volumetric shrinkage, distorting the recorded interference fringe and causing errors during the input/output of data, thereby compromising the precision of recording and reproduction (see Journal of the Japanese Society of Printing Science and Technology, 2004, Vol. 41, p. 25, which is expressly incorporated herein by reference in its entirety).

Published Japanese Translation of a PCT International Application (TOKUHYO) No. 2004-507513 or English language family member WO 02/19040, which are expressly incorporated herein by reference in their entirety, disclose the use of a cationic polymerizable monomer with little volumetric shrinkage as a recording material. However, the improvement in volumetric shrinkage is inadequate even when the technique described in Published Japanese Translation of a PCT International Application (TOKUHYO) No. 2004-507513 is employed.

Japanese Patent No. 3504884 or English language family member U.S. Pat. No. 6,124,076, which are expressly incorporated herein by reference in their entirety, disclose a method for improving volumetric shrinkage by adding a volume-expanding agent. However, in the method described in Japanese Patent No. 3504884, since the wavelength of the light employed in the reaction of the volume-expanding agent is identical to that of the recording light, in principle there is a problem in the form of reduced recording sensitivity. Accordingly, there is a need to develop a holographic recording medium of high recording and reproducing precision in which it is possible to compensate for volumetric shrinkage.

SUMMARY OF THE INVENTION

An aspect of the present invention provides for a polymerizable compound suited to the manufacturing of a holographic recording medium, especially a volume holographic recording medium, affording good recording and reproducing precision.

An aspect of the present invention relates to a polymerizable compound denoted by general formula (1).

General formula (1)

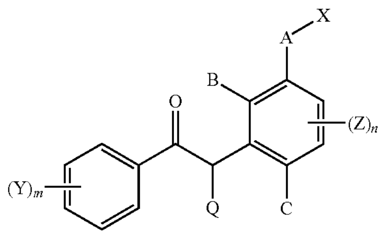

In general formula (1), A denotes an oxygen atom, sulfur atom, or NR, R denotes a hydrogen atom, alkyl group, aryl group, or heterocyclic group, X denotes a hydrogen atom, polymerizable group, optionally polymerizable group-substituted alkyl group, aryl group, or heterocyclic group, Y and Z each independently denote a halogen atom, polymerizable group, optionally polymerizable group-substituted all group, aryl group, heterocyclic group, cyano group, nitro group, hydroxy group, amino group, carboxy group, acyl group, alkoxy group, aryloxy group, acyloxy group, acylamino group, sulfonamide group, alkoxycarbonyl group, aryloxycarbonyl group, carbamoyl group, or sulfamoyl group, B and C each independently denote a hydrogen atom, halogen atom, polymerizable group, optionally polymerizable group-substituted alkyl group, aryl group, heterocyclic group, cyano group, nitro group, hydroxy group, amino group, carboxy group, acyl group, alkoxy group, aryloxy group, acyloxy group, acylamino group, sulfonamide group, alkoxycarbonyl group, aryloxycarbonyl group, carbamoyl group, or sulfamoyl group, wherein at least one from among B and C denotes a hydrogen atom and at least one from among X, Y, and Z comprises a polymerizable group, m denotes an integer ranging from 0 to 5 and plural Ys may be identical or different from each other when m is an integer of equal to or greater than 2, n denotes an integer ranging from 0 to 2 and plural Zs may be identical or different from each other when n is 2, and Q denotes an elimination group.

X in general formula (1) may be a group denoted by general formula (2).

-L-G General formula (2)

In general formula (2), L denotes a divalent linking group comprised of a combination of an alkylene group or arylene group with at least one selected from the group consisting of —O—, —S—, —C(═O)—, —$SO_2$—, —$NR^1$—, an alkylene group, and an arylene group, $R^1$ denotes a hydrogen atom or a substituent, and G denotes a polymerizable group.

A in general formula (1) may denote an oxygen atom.

Q in general formula (1) may be an elimination group denoted by general formula (3).

General formula (3)

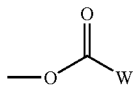

In general formula (3), W denotes an alkyl group, aryl group, or heterocyclic group.

Another aspect of the present invention relates to an optical recording composition comprising the of the above polymerizable compound.

The optical recording composition may further comprise an optical radical polymerization initiator.

The optical recording composition may further comprise a radical polymerizable monomer and/or a matrix.

The optical recording composition may be a holographic recording composition.

A further aspect of the present invention relates to a holographic recording medium comprising a recording layer, wherein the recording layer comprises the above polymerizable compound.

In the holographic recording medium, the recording layer may be formed with the above optical recording composition.

The holographic recording medium may be a volume holographic recording medium.

A further aspect of the present invention relates to a method of recording information on the above holographic recording medium. The method comprises forming an interference image on the recording layer comprised in the holographic recording medium by irradiation of an informing light and a reference light to the recording layer, and irradiating a fixing light to the recording layer on which the interference image has been formed to fix the interference image.

The informing light may have a wavelength of equal to or greater than 400 nm and the fixing light may have a wavelength of less than 400 nm.

The polymerizable compound of the present invention permits modulation of the refractive index of the recording medium following polymerization, thus permitting compensation for volumetric shrinkage of the medium resulting from the polymerization reaction. The holographic recording medium having a recording layer formed with the polymerizable compound of the present invention permits improved recording and reproducing precision.

Other exemplary embodiments and advantages of the present invention may be ascertained by reviewing the present disclosure and the accompanying drawings.

BRIEF DESCRIPTION OF THE DRAWINGS

The present invention will be described in the following text by the exemplary, non-limiting embodiments shown in the figures, wherein.

Figure 1:
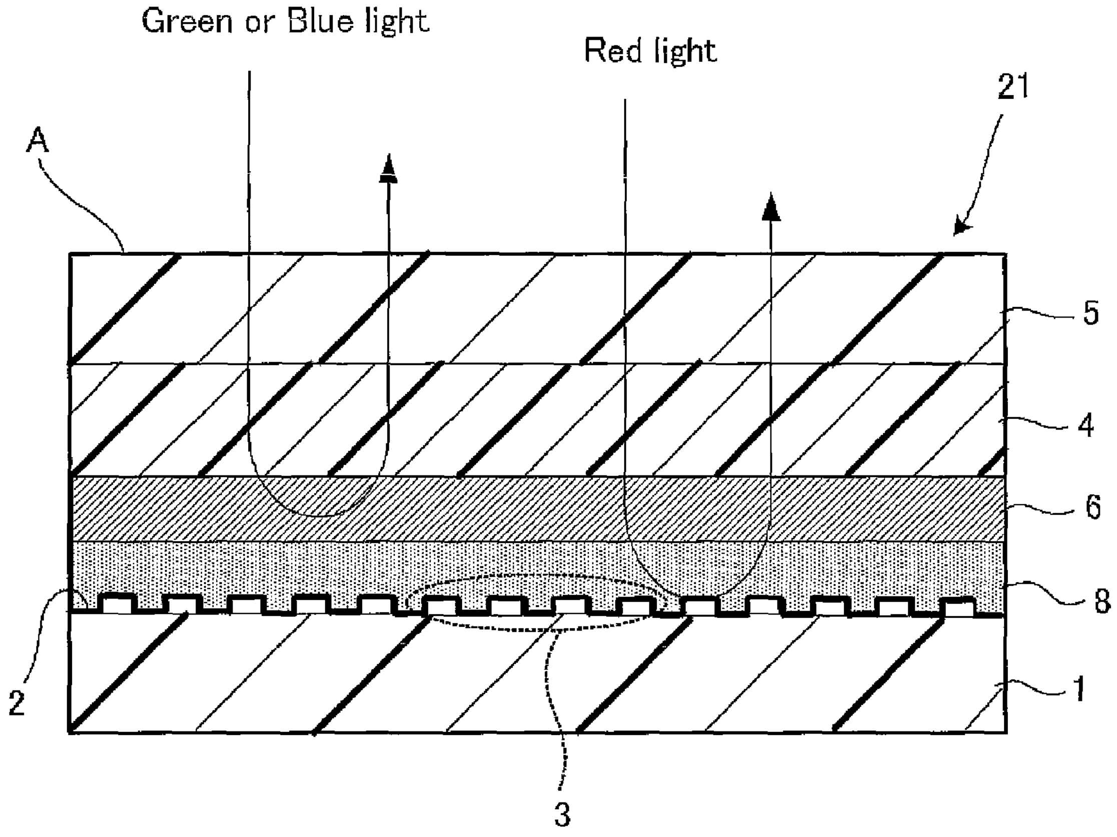
FIG. 1 is a schematic cross-sectional view of an example of a holographic recording medium according to a first implementation embodiment.

Explanations of symbols in the drawings are as follows:

1 Lower substrate
2 Reflective film
3 Servo pit pattern
4 Recording layer
5 Upper substrate
6 Filter layer
7 Second gap layer
8 First gap layer
12 Objective lens
13 Dichroic mirror
14 Detector
15 ¼ wavelength plate
16 Polarizing plate
17 Half mirror
20 Holographic recording medium
21 Holographic recording medium
22 Holographic recording medium
31 Pickup
81 Spindle
82 Spindle motor
83 Spindle servo circuit
84 Driving device
85 Detection circuit
86 Focus servo circuit
87 Tracking servo circuit
88 Slide servo circuit
89 Signal processing circuit
90 Controller
91 Operation element
100 Optical recording and reproducing device
A Entry and exit surface
FE Focus error signal
TE Tracking error signal
RF Reproduction signal

DESCRIPTIONS OF THE EMBODIMENTS

The following preferred specific embodiments are, therefore, to be construed as merely illustrative, and non-limiting to the remainder of the disclosure in any way whatsoever. In this regard, no attempt is made to show structural details of the present invention in more detail than is necessary for fundamental understanding of the present invention; the description taken with the drawings making apparent to those skilled in the art how several forms of the present invention may be embodied in practice.

Polymerizable Compound

The polymerizable compound of the present invention is denoted by general formula (1).

General formula (1)

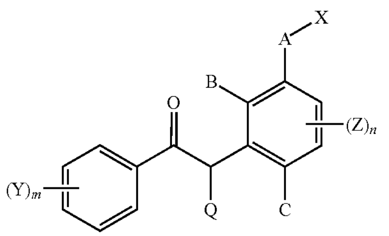

The polymerizable compound of the present invention will be described in greater detail below.

In general formula (1), A denotes an oxygen atom, sulfur atom, or NR. R denotes a hydrogen atom, alkyl group, aryl group, or heterocyclic group.

The alkyl group denoted by R may be a linear, branched, or cyclic substituted or unsubstituted alkyl group. The alkyl group is preferably a substituted or unsubstituted linear or branched alkyl group having 1 to 30 carbon atoms (such as a methyl group, ethyl group, isopropyl group, n-propyl group, n-butyl group, t-butyl group, 2-pentyl group, n-hexyl group, n-octyl group, t-octyl group, 2-ethylhexyl group, 1,5-dimethylhexyl group, n-decyl group, n-dodecyl group, n-tetradecyl group, n-hexadecyl group, hydroxyethyl group, hydroxypropyl group, 2,3-dihydroxypropyl group, carboxymethyl group, carboxyethyl group, sodium sulfoethyl group, diethylaminoethyl group, diethylaminopropyl group, butoxypropyl group, ethoxyethoxyethyl group, or n-hexyloxypropyl group); or a substituted or unsubstituted cyclic alkyl group having 3 to 18 carbon atoms (such as a cyclopropyl group, cyclopentyl group, cyclohexyl group, cyclooctyl group, adamantyl group, or cyclododecyl group). The alkyl group in the present invention further includes bicycloalkyl groups, preferably substituted or unsubstituted bicycloalkyl groups having 5 to 30 carbon atoms (that is, monovalent groups in the form of a bicycloalkane having 5 to 30 carbon atoms from which one hydrogen atom has been removed, such as bicyclo[1,2,2]heptane-2-yl and bicyclo[2,2,2]octane-3-yl) as well as tricycle structures having multiple ring structures.

The aryl group is preferably a substituted or unsubstituted aryl group having 6 to 30 carbon atoms, such as a phenyl group, p-tolyl group, naphthyl group, m-chlorophenyl group, or o-hexadecanoylaminophenyl group.

Examples of the heterocyclic group are five to seven-membered, substituted or unsubstituted, saturated or unsaturated heterocycles comprising at least one selected from among a nitrogen atom, oxygen atom, and sulfur atom. It may have a single ring, or form a condensed ring with an aryl group or heterocycle. The heterocyclic group is preferably five or six-membered, such as a pyrrolyl group, pyrrolidinyl group, pyridyl group, piperidyl group, piperazinyl group, imidazolyl group, pyrazolyl group, pyrazinyl group, pyrimidinyl group, triazinyl group, triazolyl group, tetrazolyl group, quinolyl group, isoquinolyl group, indolyl group, indazolyl group, benzoimidazolyl group, furyl group, pyranyl group, chromenyl group, thienyl group, oxazolyl group, oxadiazolyl group, thiazolyl group, thiadiazolyl group, benzooxazolyl group, benzothiazolyl group, morpholino group, or morpholinyl group.

When the above group has a substituent, the substituent may be, for example, a halogen atom (fluorine atom, chlorine atom, bromine atom, or iodine atom), alkyl group, alkenyl group, alkynyl group, aryl group, heterocyclic group, acyl group, alkoxycarbonyl group, aryloxycarbonyl group, heterocyclic oxycarbonyl group, carbamoyl group, N-hydroxycarbamoyl group, N-acylcarbamoyl group, N-sulfonylcarbamoyl group, N-carbamoylcarbamoyl group, thiocarbamoyl group, N-sulfamoylcarbamoyl group, carbazoyl group, carboxyl group (including salts thereof), oxalyl group, oxamoyl group, cyano group, formyl group, hydroxy group, alkoxy group (including a group containing repeating ethyleneoxy group or propyleneoxy group units), aryloxy group, heterocyclic oxy group, acyloxy group, alkoxycarbonyloxy group, aryloxycarbonyloxy group, carbamoyloxy group, sulfonyloxy group, silyloxy group, nitro group, amino group (alkyl, aryl, or heterocyclic) amino group, acylamino group, sulfonamide group, ureido group, thioureido group, N-hydroxyureido group, imido group, alkoxycarbonylamino group, aryloxycarbonylamino group, sulfamoylamino group, semicarbazido group, thiosemicarbazido group, hydrazino group, ammonio group, oxamoylamino group, N-(alkyl or aryl)sulfonylureido group, N-acylureido group, N-acylsulfamoylamino group, hydroxyamino group, quaternized nitrogen-containing heterocyclic group (such as a pyridinio group, imidazolio group, quinolinio group, or isoquinolinio group), isocyano group, imino group, alkylthio group, arylithio group, heterocyclic thio group, (alkyl, aryl, or heterocyclic) dithio group, (alkyl or aryl)sulfonyl group, (alkyl or aryl) sulfinyl group, sulfo group (including salts thereof), sulfamoyl group, N-acylsulfamoyl group, N-sulfonylsulfamoyl group (including salts thereof), or silyl group. In this context, the term "salt" means a salt with the cation of an alkali metal, alkaline earth metal, heavy metal, or the like, or a salt with an organic cation such as an ammonium ion, phosphonium ion, or the like. These substituents may be further substituted with the substituents mentioned above.

In general formula (1), A preferably denotes an oxygen atom or NR, more preferably an oxygen atom.

In general formula (1), X denotes a hydrogen atom, polymerizable group, optionally polymerizable group-substituted alkyl group, aryl group, or heterocyclic group. Details of the alkyl group, aryl group, or heterocyclic group denoted by X are identical to those set forth in the description of R above. In general formula (1), X preferably denotes an alkyl group, more preferably an alkyl group substituted with a polymerizable group.

Each of Y and Z independently denotes a halogen atom (such as a chlorine atom, bromine atom, or iodine atom), polymerizable group, optionally polymerizable group-substituted alkyl group, aryl group, heterocyclic group, cyano group, nitro group, hydroxy group, amino group, carboxy group, acyl group, alkoxy group, aryloxy group, acyloxy group, acylamino group, sulfonamide group (including alkyl or arylsulfonylamino group), alkoxycarbonyl group, aryloxycarbonyl group, carbamoyl group, or sulfamoyl group. Details of the alkyl groups, aryl groups, and heterocyclic groups denoted by Y and Z are identical to these set forth above in the description of R.

The amino group is preferably an unsubstituted amino group, alkylamino group having 1 to 30 carbon atoms, or anilino group having 6 to 30 carbon atoms (such as a methylamino group, dimethylamino group, anilino group, N-methylanilino group, or diphenylamino group).

The acyl group preferably denotes a substituted or unsubstituted acyl group having 2 to 30 carbon atoms (such as an acetyl group, pivanoyl group, 2-chloroacetyl group, stearoyl group, benzoyl group, or p-n-octyloxyphenylcarbonyl group).

The alkoxy group preferably denotes a substituted or unsubstituted alkoxy group having 1 to 30 carbon atoms (such as a methoxy group, ethoxy group, isopropoxy group, t-butoxy group, n-octyloxy group, or 2-methoxyethoxy group).

The aryloxy group preferably denotes a substituted or unsubstituted aryloxy group having 6 to 30 carbon atoms (such as a phenoxy group, 2-methylphenoxy group, 4-t-butylphenoxy group, 3-nitrophenoxy group, or 2-tetradecanoylaminophenoxy group).

The acyloxy group preferably denotes a formyloxy group, substituted or unsubstituted alkylcarbonyloxy group having 2 to 30 carbon atoms, or substituted or unsubstituted arylcarbonyloxy group having 6 to 30 carbon atoms (such as an acetyloxy group, pivaloyloxy group, stearoyloxy group, benzoyloxy group, or p-methoxyphenylcarbonyloxy group).

The acylamino group preferably denotes a formylamino group, substituted or unsubstituted alkylcarbonylamino group having 1 to 30 carbon atoms, or substituted or unsubstituted arylcarbonylamino group having 6 to 30 carbon atoms (such as an acetylamino group, pivanoylamino group, lauroylamino group, benzoylamino group, or 3,4,5-tri-n-octyloxyphenylcarbonylamino group).

The sulfonamide group includes an alkyl or arylsulfonylamino group, and preferably denotes a substituted or unsubstituted alkylsulfonylamino group having 1 to 30 carbon atoms or substituted or unsubstituted arylsulfonylamino group having 6 to 30 carbon atoms (such as a methylsulfonylamino group, butylsulfonylamino group, phenylsulfonylamino group, 2,3,5-trichlorophenylsulfonylamino group, or p-methylphenylsulfonylamino group).

The alkoxycarbonyl group preferably denotes a substituted or unsubstituted alkoxycarbonyl group having 2 to 30 carbon atoms (such as a methoxycarbonyl group, ethoxycarbonyl group, t-butoxycarbonyl group, or n-octadecyloxycarbonyl group).

The aryloxycarbonyl group preferably denotes a substituted or unsubstituted aryloxycarbonyl group having 7 to 30 carbon atoms (such as a phenoxycarbonyl group, o-chlorophenoxycarbonyl group, m-nitrophenoxycarbonyl group, or p-t-butylphenoxycarbonyl group).

The carbamoyl group preferably denotes a substituted or unsubstituted carbamoyl group having 1 to 30 carbon atoms (such as a carbamoyl group, N-methylcarbamoyl group, N,N-dimethylcarbamoyl group, N,N-di-n-octylcarbamoyl group, or N-(methylsulfonyl)carbamoyl group).

The sulfamoyl group preferably denotes a substituted or unsubstituted sulfamoyl group having 0 to 30 carbon atoms (such as an N-ethylsulfamoyl group, N-(3-dodecyloxypropyl)sulfamoyl group, N,N-dimethylsulfamoyl group, N-acetylsulfamoyl group, N-benzoylsulfamoyl group, or N-(N'-phenylcarbamoyl)sulfamoyl group).

In general formula (1), Y and Z preferably denote halogen atoms, optionally polymerizable group-substituted alkyl groups, cyano groups, nitro groups, hydroxy groups, amino groups, carboxy group, acyl groups, alkoxy groups, aryloxy groups, acyloxy groups, acylamino groups, alkoxycarbonyl groups, aryloxycarbonyl groups, or carbamoyl groups, more preferably denote optionally polymerizable group-substituted alkyl groups, halogen atoms, nitro groups, amino groups, alkoxy groups, aryloxy groups, acyloxy groups, acylamino groups, alkoxycarbonyl groups, aryloxycarbonyl groups, or carbamoyl groups.

In general formula (1), m denotes an integer ranging from 0 to 5, preferably a range of 0 to 2, more preferably 0 or 1, and still more preferably, 0. When m is an integer of equal to or greater than 2, plural Ys may be identical or different from each other.

In general formula (1), n denotes an integer ranging from 0 to 2. When n is 2, plural Zs may be identical or different from each other. In preferably denotes 0 or 1.

In general formula (1), at least one from among X, Y, and Z comprises a polymerizable group. In the present invention, the term "polymerizable group" means a substituent capable of polymerizing a polymerizable component by irradiation with light, by irradiation with radiation, by heating, or through the use of a radical initiator. From the perspective of not undergoing reaction in the dark, a radical polymerizable group is preferable, with a functional group capable of undergoing addition polymerization or condensation polymerization being preferred. Specific examples of the polymerizable groups are given below.

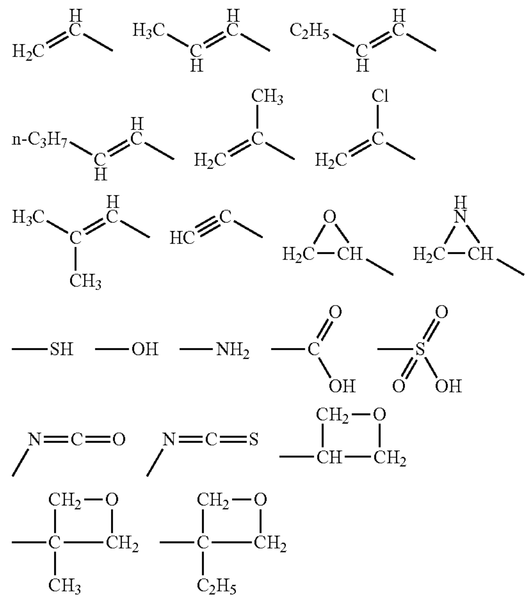

The polymerizable group is preferably a functional group capable of undergoing addition polymerization. Preferable examples of such polymerizable groups are polymerizable ethylenic unsaturated groups and ring-opening polymerizable groups; More preferable examples are radical polymerizable groups in the form of polymerizable ethylenic unsaturated groups. The groups denoted by formulas (M-1) to (M-6) below are examples of radical polymerizable groups.

(M-1)

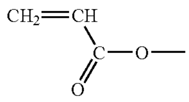

(M-2)

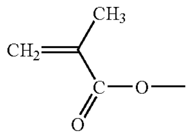

-continued (M-3)

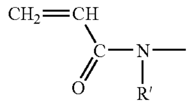

(M-4)

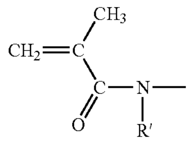

(M-5)

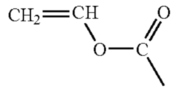

(M-6)

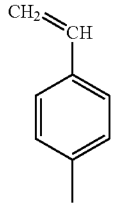

In formulas (M-3) and (M-4), R' denotes a hydrogen atom or an alkyl group, preferably a hydrogen atom or methyl group. The polymerizable group is preferably the group denoted by formula (M-1) or (M-2), with the group denoted by formula (M-1) being particularly preferred.

In general formula (1), X preferably denotes a group denoted by general formula (2) below.

-L-G General formula (2)

General formula (2) will be described below.

In general formula (2), L denotes a divalent linking group comprised of a combination of an alkylene group or arylene group with at least one selected from the group consisting of —O—, —S—, —C(═O)—, —$SO_2$—, —$NR^1$—, an alkylene group, and an arylene group, $R^1$ denotes a hydrogen atom or a substituent, and G denotes a polymerizable group.

L preferably denotes a divalent linking group comprised of a combination of an alkylene group with at least one selected from the group consisting of —O—, —C(═O)—, —$NR^1R$—, and an arylene group, more preferably a divalent linking group comprised of a combination of an alkylene group with at least one selected from the group consisting of —O—, —C(═O)—, and —$NR^1$—.

G denotes a polymerizable group, and details thereof are the same as those described above for the polymerizable groups that may be present on X, Y or Z. The preferred examples are also identical to those described above for the polymerizable groups that may be present on X, Y, or Z.

B and C each independently denote a hydrogen atom, halogen atom, polymerizable group, optionally polymerizable group-substituted alkyl group, aryl group, heterocyclic group, cyano group, nitro group, hydroxy group, amino group, carboxy group, acyl group, alkoxy group, aryloxy group, acyloxy group, acylamino group, sulfonamide group, alkoxycarbonyl group, aryloxycarbonyl group, carbamoyl group, or sulfamoyl group. At least one from among B and C denotes a hydrogen atom. Details of the halogen atoms and substituents denoted by B and C are identical to those set forth above for Y and Z.

Each of B and C preferably independently denotes a hydrogen atom, halogen atom, optionally polymerizable group-substituted alkyl group, cyano group, nitro group, hydroxy group, amino group, carboxy group, acyl group, alkoxy group, aryloxy group, acyloxy group, acylamino group, alkoxycarbonyl group, aryloxycarbonyl group, or carbamoyl group; and more preferably denotes a hydrogen atom, halogen atom, optionally radical polymerizable group-substituted alkyl group, nitro group, amino group, alkoxy group, aryloxy group, acyloxy group, acylamino group, alkoxycarbonyl group, aryloxycarbonyl group, or carbamoyl group. Still more preferably; B and C both denote hydrogen atoms.

In general formula (1), Q denotes an elimination group. In the present invention, the term "elimination group" means a Q such that the pKa value of the compound denoted by Q-H is equal to or less than 10. In this context, the term "pKa" is a quantitative indicator of the strength of an acid; it is defined as the negative common logarithm of the equilibrium constant Ka for a dissociation reaction in which a hydrogen ion ($H^+$) is released from Q-H. Specific examples of the elimination group denoted by Q are: acyloxy groups, alkylsulfonyloxy groups, arylsulfonyloxy groups, halogen atoms such as chlorine, bromine, and iodine, aryloxy groups, and arylthio groups. Preferable examples are acryloxy groups, alkylsulfonyloxy groups, arylsulfonyloxy groups, and arylthio groups. More preferable examples are acyloxy groups, alkylsulfonyloxy groups, and arylsulfonyloxy group. Acyloxy groups are of even greater preference.

Q is preferably an elimination group denoted by general formula (3) below.

General formula (3)

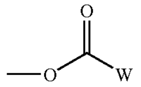

In general formula (3), W denotes an alkyl group, aryl group, or heterocyclic group. Details of the alkyl group, aryl group, and heterocyclic group denoted by W are identical to those set forth above in the description of R. W preferably denotes an alkyl group or an aryl group.

A preferable embodiment of the compound denoted by general formula (1) is a compound in which A denotes an oxygen atom and Q denotes the elimination group denoted by general formula (3). In the compound denoted by general formula (1), one to three polymerizable groups are preferably present per molecule, with the presence of one or two such groups being preferred. The polymerizable group is contained in at least one of the groups denoted by X, Y, and Z, and is preferably contained in at least the group denoted by X and/or Z.

Specific examples of the compound denoted by general formula (1) are given below. However, the present invention is not limited thereto.

(Example Compounds)

RR-1

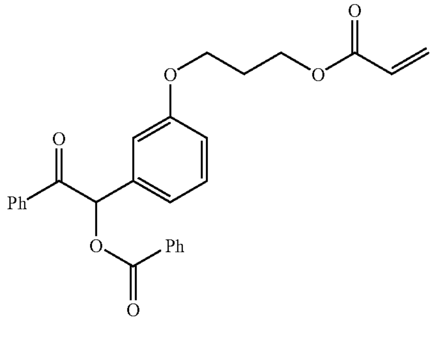

-continued
RR-2
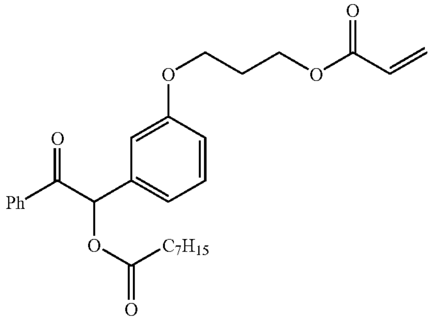
RR-3
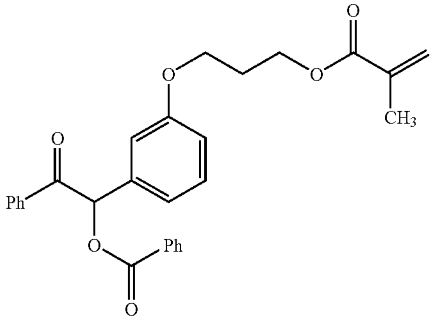
RR-4
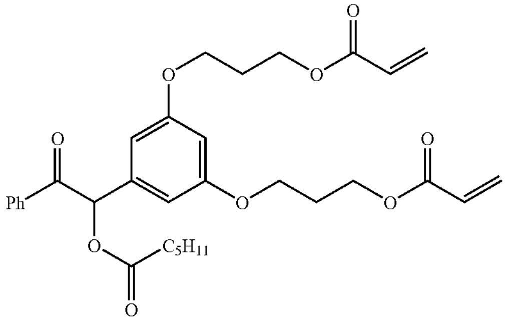
RR-5
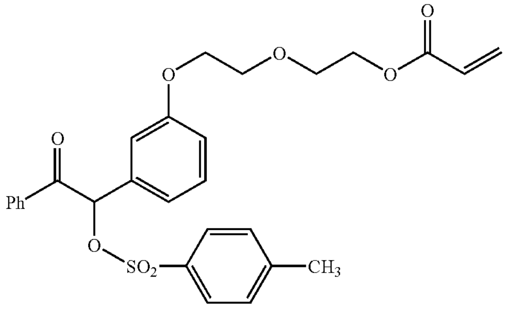
RR-6
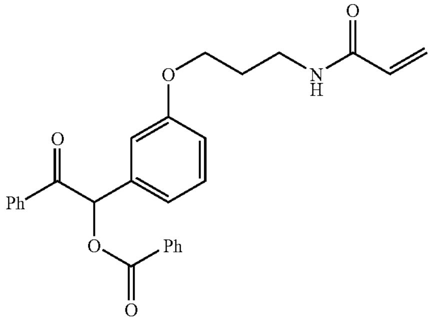
-continued
RR-7
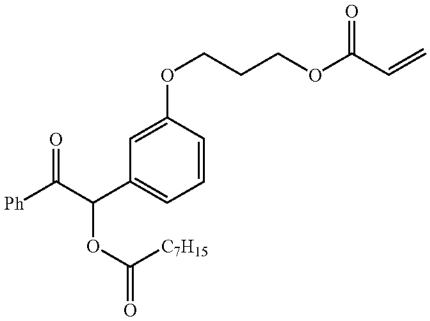
RR-8
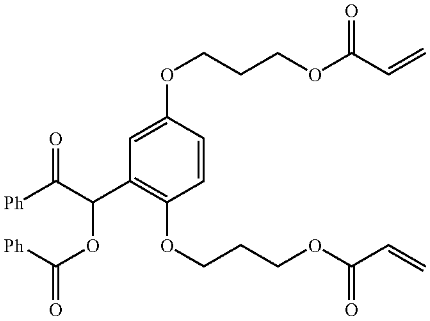
RR-9
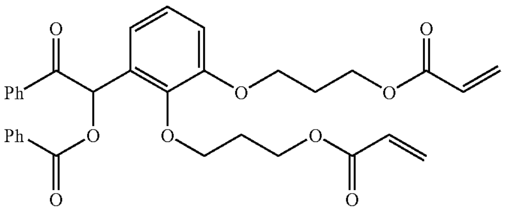
RR-10
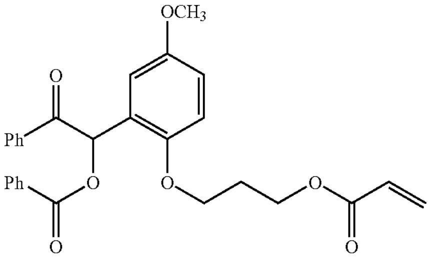
RR-11
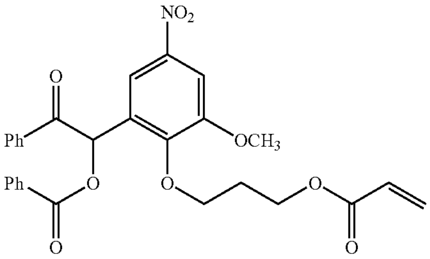

-continued
RR-12
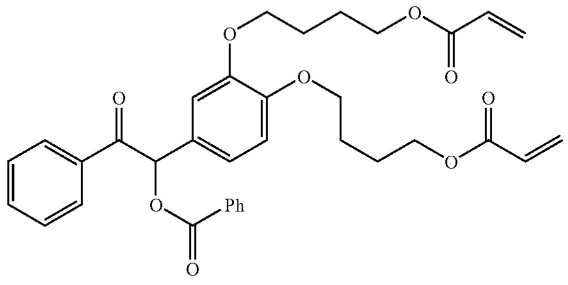
RR-13
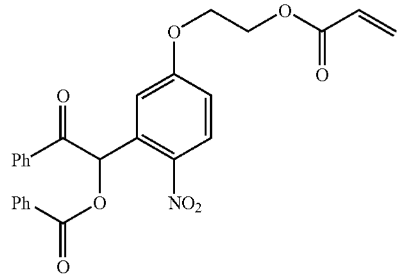
RR-14
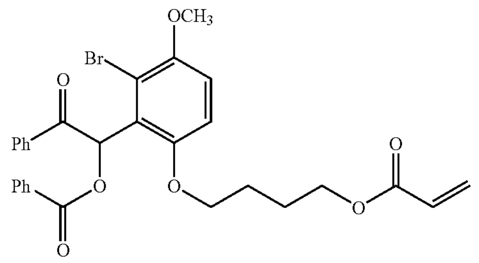
RR-15
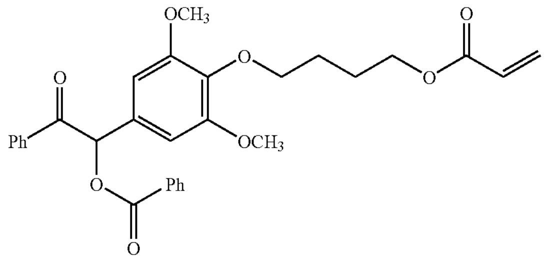
RR-16
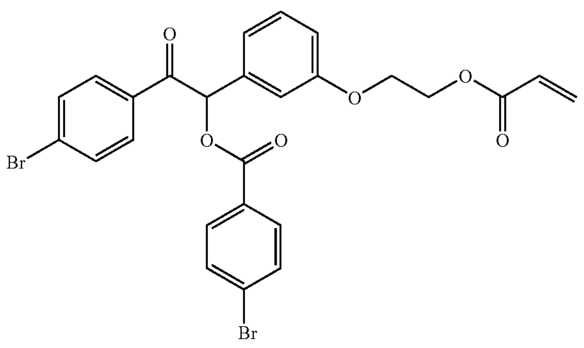
-continued
RR-17
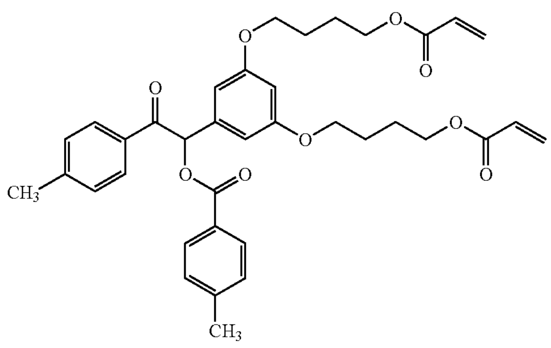
RR-18
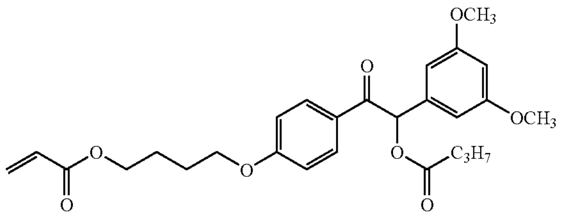
RR-19
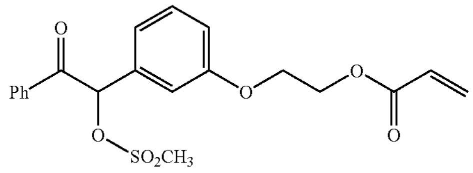
RR-20
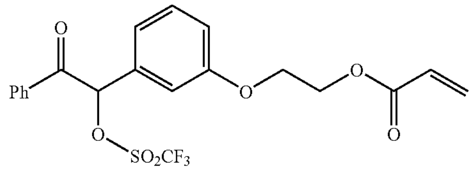
RR-21
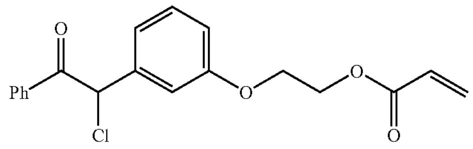
RR-22
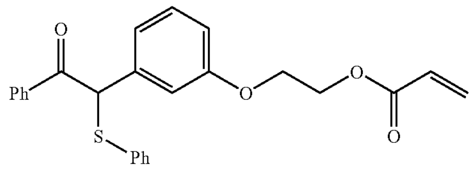
RR-23
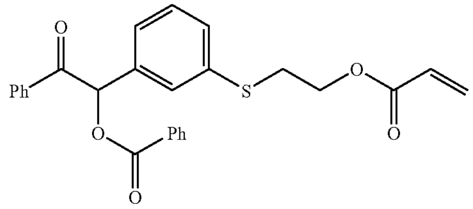

-continued
RR-24
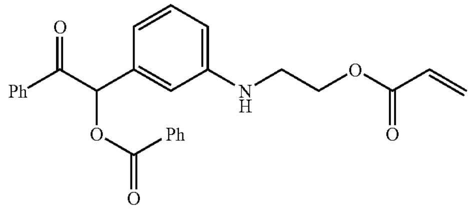
RR-25
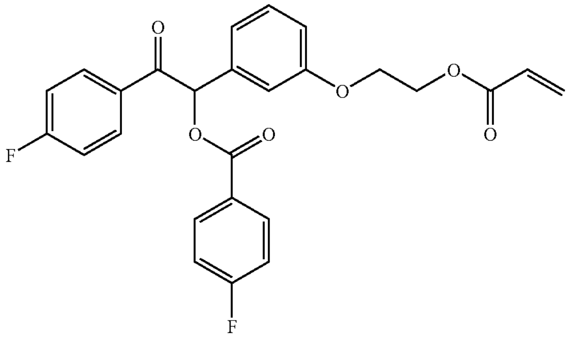
RR-26
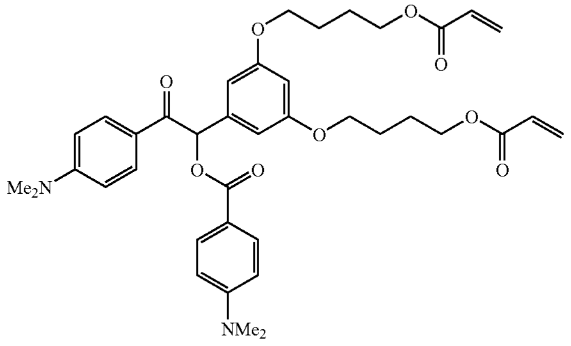
RR-27
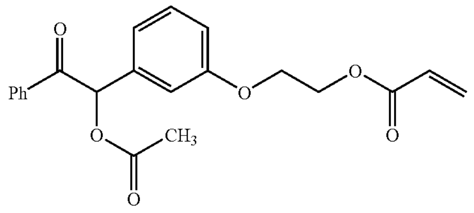
RR-28
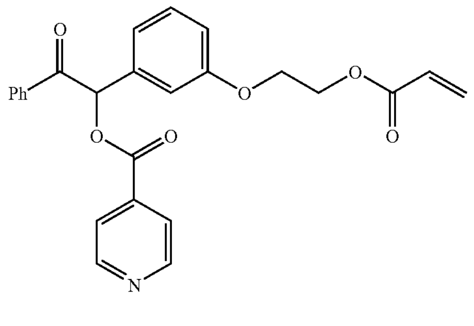
-continued
RR-29
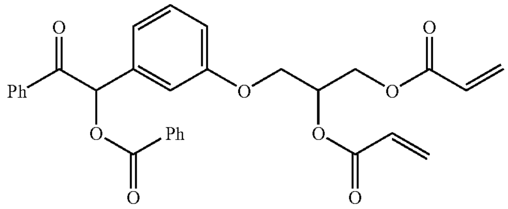
RR-30
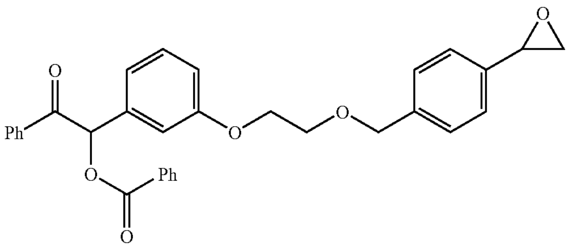
RR-31
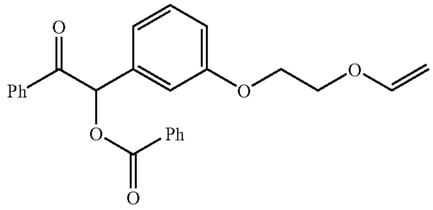
RR-32
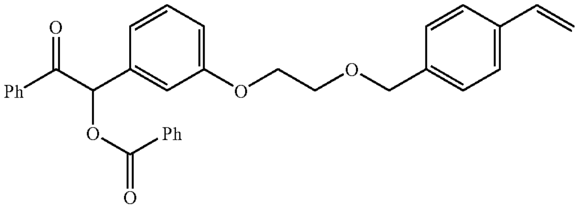
RR-33
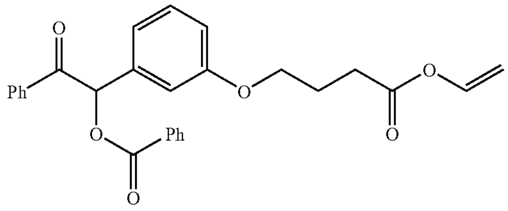
RR-34
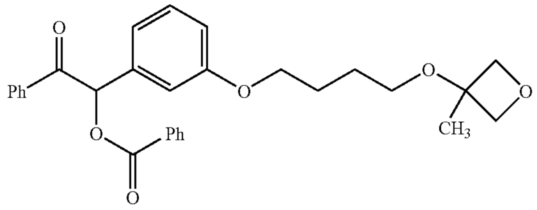

-continued

RR-35

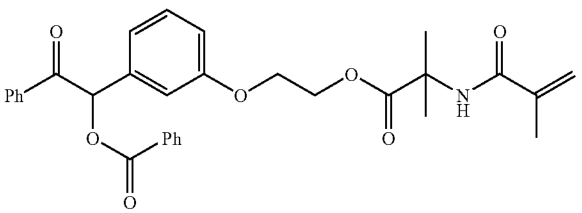

RR-36

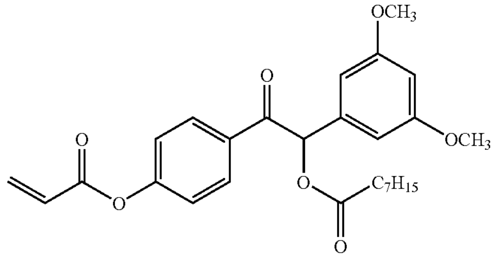

The compound denoted by general formula (1) can be synthesized by one or combination of various known methods; suitable synthesis methods can be selected based on the individual compound. For synthesis methods, reference may be made to the descriptions given in, for example, the Journal of the American Chemical Society, 1971, Vol. 93, p. 7222, and Tetrahedron, 2004, Vol. 60, p. 3,803, which is expressly incorporated herein by reference in its entirety.

Optical Recording Composition

The optical recording composition of the present invention comprises the polymerizable composition of the present invention, is preferably employed as a holographic recording composition, and is particularly suitable as a volume holographic recording composition. As set forth above, holographic recording is a method of recording information by superposing an informing light containing information and a reference light in a recording layer to write an interference fringe thus formed in the recording layer. Volume holographic recording is a method of recording information in holographic recording in which a three-dimensional interference image is written in the recording layer.

In the radical polymerizable monomers that have been conventionally employed as recording materials in holographic recording compositions, volumetric shrinkage of the recording medium occurs with the progression of monomer polymerization during recording and fixation. Recording media containing such radical polymerizable monomers present problems; volumetric shrinkage causes errors, because the conditions for reading with the reference light do not reproduce the recording light, making it difficult to accurately read recorded data. In this context, the length of the optical path as the recording light and reference light pass through the recording medium is given by the "refractive index of the medium multiplied by its geometric length." It is thought that the conditions for reading with the reference light do not reproduce the recording light because volumetric shrinkage of the medium reduces the "geometric length," rendering the length of the optical path of the reference light shorter than the length of the optical path of the recording light.

The present inventors conducted extensive research into resolving the above-stated problems, resulting in the discovery that the problem of reduced reading precision due to volumetric shrinkage was solved by increasing the "refractive index of the medium" by the amount of reduction in "geometric length" due to volumetric shrinkage. The present inventors conducted further extensive research based on this discovery, further discovering that use of the compound denoted by general formula (1) as the recording material solved the above-stated problem; the present invention was devised on this basis. This point will be described in greater detail below.

The compound denoted by general formula (1) is structurally characterized in that the substituent denoted by -A-X is present at the meta position as well as a hydrogen atom is present at at least one of ortho positions of an aromatic ring, and is also characterized in that irradiation with ultraviolet (UV) radiation (wavelength <400 nm) induces a photoreaction producing a benzofuran derivative.

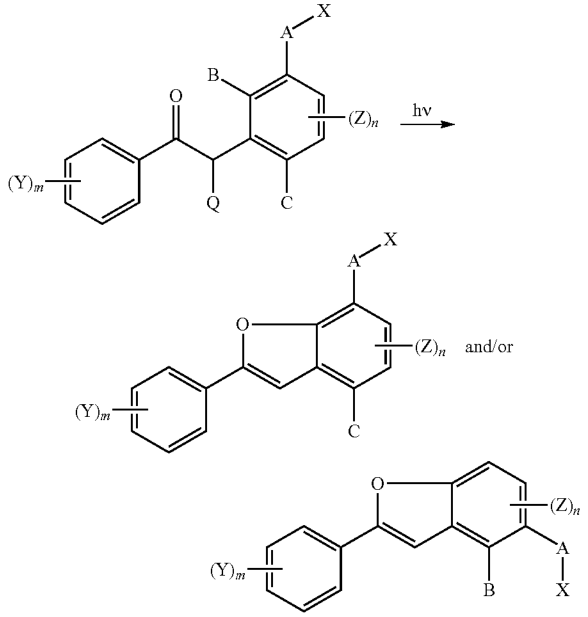

When the compound denoted by general formula (1) is converted to a benzofuran derivative, the absorption wavelength of the compound increases and the refractive index increases due to the Kramers-Krong relation. That is, once information has been recorded (at a recording wavelength of ≧400 nm) by irradiation with the recording light in a holographic recording medium containing the compound of general formula (1), irradiation with a fixing light with a wavelength of <400 nm, for example, generates a benzofuran derivative. With this generation comes an increase in the refractive index. That is, increasing the "refractive index of the medium" can compensate for the amount of reduction in "geometric length" accompanying volumetric shrinkage. As a result, the length of the optical path of the reference light can become identical to the length of the optical path of the recording light, permitting accurate reading of recorded data.

The optical recording composition of the present invention comprises at least the compound denoted by general formula (1). The content of the compound denoted by general formula (1) in the optical recording composition of the present invention is, for example, 1 to 50 weight percent, preferably 1 to 30 weight percent, and more preferably, 1 to 10 weight percent.

The optical recording composition of the present invention may comprise an optical radical polymerization initiator in addition to the compound denoted by general formula (1). As needed, a radical polymerizable monomer or matrix, as well as other components, may be further incorporated.

Examples of such optical radical polymerization initiators are materials that undergo radical reactions when irradiated with light. A compound that is sensitive to the informing light employed to record information in the recording medium formed with the optical recording composition of the present invention is preferable. Examples of such optical radical polymerization initiators are: 2,2'-bis(o-chlorophenyl)-4,4'-5,5'-tetraphenyl-1,1'-biimidazole, 2,4,6-tris(trichloromethyl)-1,3,5-triazine, 2,4-bis(trichloromethyl)-6-(p-methoxyphenylvinyl)-1,3,5-triazine, diphenyliodoniumtetrafluoroborate, diphenyliodonium-hexafluorophosphate, 4,4'-di-t-butyldiphenyliodoniumtetrafluoroborate, 4-diethylaminophenylbenzenediazoniumhexafluorophosphate, benzoin, 2-hydroxy-2-methyl-1-phenylpropane-2-one, benzophenone, thioxanthone, 2,4,6-trimethylbenzoyl diphenylacyl phosphine oxide, triphenylbutylborate tetraethyl ammonium, diphenyl-4-phenylthiophenyl sulfonium hexafluorophosphate, 2,2-dimethoxy-1,2-diphenylethane-1-one, phenylglyoxylic acid methyl ester, 2-methyl-1-[4-(methylthio)phenyl]-2-morpholinopropane-1-one, bis(2,4,6-trimethylbenzoyl)phenylphosphine oxide, 2,4,6-trimethylbenzoyl diphenyl phosphine oxide, 1,2-octanedione, 1-[4-(phenylthio)-2-(O-benzoyloxime)], and bis(eta 5-2,4-cyclopentadien-1-yl)bis[2,6-difluoro-3-(1H-pyrrol-1-yl)phenyltitanium]. These may be employed singly or in combinations of two or more. A sensitizing dye, described further below, may also be employed in combination based on the wavelength of the light being irradiated.

The content of the optical radical polymerization initiator in the optical recording composition is preferably 0.01 to 5 weight percent, more preferably 1 to 3 weight percent.

Examples of radical polymerizable monomers are radical polymerizable monomers having unsaturated bonds such as acrylic groups, methacrylic groups, styryl groups, and vinyl groups. These monomers may be monofunctional or multifunctional. They may be employed singly, or in combinations of two or more with other monomers. Examples of such radical polymerizable monomers are: acryloylmorpholine, phenoxyethyl acrylate, isobornyl acrylate, 2-hydroxypropyl acrylate, 2-ethylhexyl acrylate, 1,6-hexanediol diacrylate, tripropylene glycol diacrylate, neopentyl glycol PO-modified diacrylate, 1,9-nonanediol diacrylate, hydroxypivalic acid neopentyl glycol diacrylate, EO-modified bisphenol A diacrylate, polyethylene glycol diacrylate, pentaerytritol triacrylate, pentaerythritol tetraacrylate, pentaerythritol hexaacrylate, EO-modified glycerol triacrylate, trimethylol propane triacrylate, EO-modified trimethylol propane triacrylate, 2-naphtho-1-oxyethyl acrylate, 2-carbazoyl-9-ylethyl acrylate, (trimethylsilyloxy)dimethylsilylpropyl acrylate, vinyl-1-naphthoate, 2,4,6-tribromophenyl acrylate, pentabromoacrylate, phenylthioethyl acrylate, tetrahydrofurfuryl acrylate, bisphenoxyethanolfluorene diacrylate, styrene, p-chlorostyrene, N-vinylcarbazole, N-vinylpyrrolidone. Of these, phenoxyethyl acrylate, 2,4,6-tribromophenyl acrylate, pentabromoacrylate, and bisphenloxyethanolfluorene diacrylate are preferable and 2,4,6-tribromophenyl acrylate and bisphenoxyethanolfluorene diacrylate are more preferable.

The content of the radical polymerizable monomer in the optical recording composition is preferably 1 to 50 weight percent, more preferably 1 to 30 weight percent, and further preferably, 3 to 10 weight percent. When the content is equal to or less than 50 weight percent, a stable interference image can be obtained. At equal to or greater than 1 weight, properties that are desirable from the viewpoint of diffraction efficiency can be obtained. However, the content of the radical polymerizable monomer is not limited to these ranges, and may be suitably adjusted based on the objective.

The "matrix" means a polymer that is capable of holding photopolymerization initiators and monomers related to the recording and storage of information and that can be employed for achieving enhanced coating properties, coating strength, and hologram recording characteristics.

The matrix is not specifically limited and may be suitably selected based on the objective. However, a thermosetting matrix is desirable, such as a urethane resin formed from an isocyanate compound and an alcohol compound; and polymers obtained by polymerizing epoxy compounds formed from oxirane compounds, melamine compounds, formalin compounds, compounds in the form of esters of (meth)acrylic acid, itaconic acid, and other unsaturated acids, and amide compounds. These polymers may be cured by heat, or photocured using a catalyst or the like. Of these, polyurethane matrixes formed from isocyanate compounds and alcohol compounds are preferable. Considering its ability to retain recordings, a three-dimensional polyurethane matrix formed from polyhydric isocyanate and a polyhydric alcohol is particularly preferred.

A specific example of a polyhydric isocyanate and a polyhydric alcohol capable of forming a polyurethane matrix will be set forth below.

Specific examples of the above polyhydric isocyanate are: biscyclohexylmethane diisocyanate, hexamethylene diisocyanate, phenylene-1,3-diisocyanate, phenylene-1,4-diisocyanate, 1-methoxyphenylene-2,4-diisocyanate, 1-methylphenylene-2,4-diisocyanate, 2,4-tolylene diisocyanate, 2,6-tolylene diisocyanate, 1,3-xylylene diisocyanate, 1,4-xylylene diisocyanate, biphenylene-4,4'-diisocyanate, 3,3'-dimethoxybiphenylene-4,4'-diisocyanate, 3,3'-dimethylbiphenylene-4,4'-diisocyanate, diphenylmethane-2,4'-diisocyanate, diphenylmethane-4,4'-diisocyanate, 3,3'-dimethoxydiphenylmethane-4,4'-diisocyanate, 3,3'-dimethyldiphenylmethane-4,4'-diisocyanate, naphthylene-1,5-diisocyanate, cyclobutylene-1,3'-diisocyanate, cyclopentylene-1,3-diisocyanate, cyclohexylene-1,3-diisocyanate, cyclohexylene-1,4-diisocyanate, 1-methylcyclohexylene-2,4-diisocyanate, 1-methylcyclohexylene-2,6-diisocyanate, 1 isocyanate-3,3,5-trimethyl-5-isocyanate methylcyclohexane, cyclohexane-1,3-bis(methylisocyanate), cyclohexane-1,4-bis(methylisocyanate), isophorone diisocyanate, dicyclohexylmethane-2,4'-diisocyanate, dicyclohexylmethane-4,4'-diisocyanate, ethylene diisocyanate, tetramethylene-1,4-diisocyanate, hexatnethylene-1,6-diisocyanate, dodecamethylene-1,12-diisocyanate, phenyl-1,3,5-triisocyanate, diphenylmethane-2,4,4'-triisocyanate, diphenylmethane-2,5,4'-triisocyanate, triphenylmethane-2,4',4"-triisocyanate, triphenylmethane-4,4',4"-triisocyanate, diphenylmethane-2,4,2',4'-tetraisocyanate, diphenylmethane-2,5,2',5'-tetraisocyanate, cyclohexane-1,3,5-triisocyanate, cyclohexane-1,3,5-tris(methylisocyanate), 3,5-dimethylcyclohexane-1,3,5-tris(methylisocyanate), 1,3,5-trimethylcyclohexane-1,3,5-tris(methylisocyanate), dicyclohexylmethane-2,4,2'-triisocyanate, dicyclohexylmethane-2,4,4'-triisocyanate lysine diisocyanate methyl ester, and two-terminal isocyanate prepolymers obtained by reacting a stoichiometrically excess quantity of an organic isocyanate compound of one of the preceding with a multifunctional active hydrogen-containing compound. Of these, biscyclohexylmethane diisocyanate and hexamethylene diisocyanate are preferred. They may be employed singly or in combinations of two or more.

The above polyhydric alcohol may be in the form of a polyhydric alcohol alone, or in the form of a mixture with another multifunctional alcohol. Examples of polyhydric alcohols are: glycols such as ethylene glycol, triethylene glycol, diethylene glycol, polyethylene glycol, propylene glycol, polypropylene glycol, and neopentyl glycol; diols such as butanediol, pentanediol, hexanediol, heptanediol, and tetramethylene glycol; bisphenols and compounds obtained by modifying such polyfunctional alcohols with a polyethyleneoxy or polypropyleneoxy chain; triols such as glycerin, trimethylol propane, butanetriol, pentanetriol, hexanetriol, and decanethiol; and compounds obtained by modifying such polyfunctional alcohols with a polyethyleneoxy or polypropyleneoxy chain.

The content of the matrix in the optical recording composition is preferably 10 to 95 weight percent, more preferably 35 to 90 weight percent. When the content is equal to or greater than 10 weight percent, a stable interference image can be obtained. When equal to or less than 95 weight percent, desirable properties from the perspective of diffraction efficiency can be obtained.

Polymerization inhibitors and oxidation inhibitors may be added to the optical recording composition of the present invention to improve the storage stability of the optical recording composition.

Examples of polymerization inhibitors and oxidation inhibitors are: hydroquinone, p-benzoquinone, hydroquinone monomethyl ether, 2,6-ditert-butyl-p-cresol, 2,2'-methylenebis(4-methyl-6-tert-butylphenol), triphenylphosphite, trisnonylphenylphoshite, phenothiazine, and N-isopropyl-N'-phenyl-p-phenylenediamine.

The quantity of polymerization inhibitor or oxidation inhibitor added is preferably equal to or less than 3 weight percent of the total quantity of radical polymerizable monomer. When the quantity added exceeds 3 weight percent, polymerization may slow down, and in extreme cases, ceases.

As needed, a sensitizing dye may be added to the optical recording composition of the present invention. Known compounds such as those described in "Research Disclosure, Vol. 200, 1980, December, Item 20036" and "Sensitizers" (pp. 160-163, Kodansha, ed. by K. Toklumaru and M. Okawara, 1987) and the like may be employed as sensitizing dyes.

Specific examples of sensitizing dyes are: 3-ketocoumarin compounds described in Japanese Unexamined Patent Publication (KOKAI) Showa No. 58-15603; thiapyrilium salt described in Japanese Unexamined Patent Publication (KOKAI) Showa No. 58-40302; naphthothiazole merocyanine compounds described in Japanese Examined Patent Publications (KOKOKU) Showa Nos. 59-28328 and 60-53300; and merocyanine compounds described in Japanese Examined Patent Publications (KOKOKU) Showa Nos. 61-9621 and 62-3842 and Japanese Unexamined Patent Publications (KOKAI) Showa Nos. 59-89303 and 60-60104, which are expressly incorporated herein by reference in their entirety.

Further examples are the dyes described in "The Chemistry of Functional Dyes" (1981, CMC Press, pp. 393-416) and "Coloring Materials" (60 [4] 212-224 (1987)), which are expressly incorporated herein by reference in their entirety. Specific examples are cationic methine dyes, cationic carbonium dyes, cationic quinoneimine dyes, cationic indoline dyes, and cationic styryl dyes.

Further, keto dyes such as coumarin (including ketocoumarin and sulfonocoumarin) dyes, merostyryl dyes, oxonol dyes, and hemioxonol dyes; nonketo dyes such as nonketo polymethine dyes, triarylmethane dyes, xanthene dyes, anthracene dyes, rhodamine dyes, acrylidine dyes, aniline dyes, and azo dyes; nonketo polymethine dyes such as azomethine dyes, cyanine dyes, carbocyanine dyes, dicarbocyanine dyes, tricarbocyanine dyes, hemicyanine dyes, and styryl dyes; and quinone imine dyes such as azine dyes, oxazine dyes, thiazine dyes, quinoline dyes, and thiazole dyes are included among the spectral sensitizing dyes.

These sensitizing dyes may be employed singly or in combinations of two or more. From the perspectives of diffraction efficiency, sensitivity, and recording density (degree of multiplexing), the recording layer in the holographic recording medium preferably has a transmittance of 10 to 99 percent, more preferably 20 to 95 percent, further preferably 30 to 90 percent, and still more preferably, 40 to 85 percent for the recording wavelength light. Accordingly, to achieve a recording layer with such a transmittance, the mole concentration of sensitizing dye that is added is desirably adjusted to the recording wavelength in a manner conforming to the thickness of the recording layer.

A photo-heat converting material can be incorporated into the optical recording composition of the present invention for enhancing the sensitivity of the recording layer formed with the optical recording composition of the present invention.

The photo-heat converting material is not specifically limited, and may be suitably selected based on the functions and properties desired. For example, for convenience during addition to the recording layer with the compound denoted by general formula (1) and so as not to scatter incident light, an organic dye or pigment is desirable. From the perspectives of not absorbing and not scattering light from the light source employed in recording, infrared radiation-absorbing dyes are desirable.

Such infrared radiation-absorbing dyes are not specifically limited, and may be suitably selected based on the objective. However, cationic dyes, complex-forming dyes, quinone-based neutral dyes, and the like are suitable. The maximum absorption wavelength of the infrared radiation-absorbing dye preferably falls within a range of 600 to 1,000 nm, more preferably a range of 700 to 900 nm.

The content of infrared radiation-absorbing dye in the optical recording composition of the present invention can be determined based on the absorbance at the wavelength of maximum absorbance in the infrared region in the recording medium formed with the optical recording composition of the present invention. This absorbance preferably falls within a range of 0.1 to 2.5, more preferably a range of 0.2 to 2.0.

The optical recording composition of the present invention can be employed as various holographic recording compositions capable of recording information when irradiated with a light containing information. In particular, it is suited to use as a volume holographic recording composition. The recording layer can be formed by casting when the viscosity of the optical recording composition is adequately low. When the viscosity is so high that casting is difficult, a dispenser can be employed to spread a recording layer on a lower substrate, and an upper substrate pressed onto the recording layer so as to cover it and spread it over the entire surface, thereby forming a recording medium.

Holographic Recording Medium

The holographic recording medium of the present invention comprises a recording layer comprising the polymerizable compound of the present invention. The recording layer can be formed with the optical recording composition of the present invention. For example, the recording layer comprised of the optical recording composition of the present invention can be formed by the above-described method.

The holographic recording medium of the present invention comprises the above recording layer holographic recording layer), and preferably comprises a lower substrate, a filter layer, a holographic recording layer, and an upper substrate. As needed, it may comprise additional layers such as a reflective layer, filter layer, first gap layer, and second gap layer.

The holographic recording medium of the present invention is capable of recording and reproducing information through utilization of the principle of the hologram. This may be a relatively thin planar hologram that records two-dimensional information or the like, or a volumetric hologram that records large quantities of information, such as three-dimensional images. It may be either of the transmitting or reflecting type. Since the holographic recording medium of the present invention is capable of recording high volumes of information, it is suitable for use as a volume holographic recording medium of which high recording density is demanded.

The method of recording a hologram on the holographic recording medium of the present invention is not specifically limited; examples are amplitude holograms, phase holograms, blazed holograms, and complex amplitude holograms. Among these, a preferred method is the so-called "collinear method" in which recording of information in volume holographic recording regions is carried out by irradiating an informing light and a reference light onto a volume holographic recording area as coaxial beams to record information by means of interference pattern through interference of the informing light and the reference light.

Details of substrates and various layers that can be incorporated into the holographic recording medium of the present invention will be described below.

—Substrate—

The substrate is not specifically limited in terms of its shape, structure, size, or the like; these may be suitably selected based on the objective. For example, the substrate may be disk-shaped, card-shaped, or the like. A substrate of a material capable of ensuring the mechanical strength of the holographic recording medium can be suitably selected. When the light employed for recording and reproducing enters after passing through the substrate, a substrate that is adequately transparent at the wavelength region of the light employed is desirable.

Normally, glass, ceramic, resin, or the like is employed as the substrate material. From the perspectives of moldability and cost, resin is particularly suitable. Examples of such resins are: polycarbonate resin, acrylic resin, epoxy resin, polystyrene resin, acrylonitrile—styrene copolymers, polyethylene resin, polypropylene resin, silicone resin, fluorine resin, ADS resin, and urethane resin. Of these, from the perspective of moldability, optical characteristics, and cost, polycarbonate resin and acrylic resin are preferred. Synthesized resins and commercially available resins may both be employed as substrates.

Normally, address servo areas are provided on the substrate at prescribed angular intervals as multiple positioning areas extending linearly in a radial direction, with the fan-shaped intervals between adjacent address servo areas serving as data areas. Information for operating focus servos and tracking servos by the sampled servo method, as well as address information, is recorded (preformatted) as pre-embossed pits (servo pits) or the like in address servo areas. Focus servo operation can be conducted using the reflective surface of a reflective film. Wobble pits, for example, can be employed as information for operating a tracking servo. When the holographic recording medium is card-shaped, it is possible not to have a servo pit pattern.

The thickness of the substrate is not specifically limited, and may be suitably selected based on the objective: a thickness of 0.1 to 5 mm is preferable, with 0.3 to 2 mm being preferred. A substrate thickness of equal to or greater than 0.1 mm is capable of preventing shape deformation during disk storage, while a thickness of equal to or less than 5 mm can avoid an overall disk weight generating an excessive load on the drive motor.

—Recording Layer—

The recording layer can be formed with the optical recording composition of the present invention and is capable of recording information by holography. The thickness of the recording layer is not specifically limited, and may be suitably selected based on the objective. A recording layer thickness falling within a range of 1 to 1,000 micrometers yields an adequate S/N ratio even when conducting 10 to 300 shift multiplexing, and a thickness falling within a range of 100 to 700 micrometers is advantageous in that it yields a markedly good S/N ratio.

—Reflective Film—

A reflective film can be formed on the servo pit pattern surface of the substrate.

A material having high reflectance for the informing light and reference light is preferably employed as the material of the reflective film. When the wavelength of the light employed as the informing light and reference light ranges from 400 to 780 nm, examples of desirable materials are Al, Al alloys, Ag, and Ag alloys. When the wavelength of the light employed as the informing light and reference light is equal to or greater than 650 nm, examples of desirable materials are Al, Al alloys, Ag, Ag alloys, Au, Cu alloys, and TiN.

By employing an optical recording medium that reflects light as well as can be recorded and/or erased information such as a DVD (digital video disk) as a reflective film, it is possible to record and rewrite directory information, such as the areas in which holograms have been recorded, when rewriting was conducted, and the areas in which errors are present and for which alternate processing has been conducted, without affecting the hologram.

The method of forming the reflective film is not specifically limited and may be suitably selected based on the objective. Various vapor phase growth methods such as vacuum deposition, sputtering, plasma CVD, optical CVD, ion plating, and electron beam vapor deposition may be employed. Of these, sputtering is superior from the perspectives of mass production, film quality, and the like.

The thickness of the reflective film is preferably equal to or greater than 50 nm, more preferably equal to or greater than 100 nm, to obtain adequate reflectance.

—Filter Layer—

A filter layer can be provided on the servo pits of the substrate, on the reflective layer, or on the first gap layer, described further below.

The filter layer has a function of reflecting selective wavelengths in which, among multiple light rays, only light of a specific wavelength is selectively reflected, permitting passing one light and reflecting a second light. It also has a function of preventing generation of noise in which irregular reflection of the informing light and the reference light by the reflective film of the recording medium is prevented without a shift in the selectively reflected wavelength even when the angle of incidence varies. Therefore, by stacking filter layers on the recording medium, it is possible to perform optical recording with high resolution and good diffraction efficiency.

The filter layer is not specifically limited and may be suitably selected based on the objective. For example, the filter layer can be comprised of a laminate in which at least one of a dichroic mirror layer, coloring material-containing layer, dielectric vapor deposition layer, single-layer or two- or more layer cholesteric layer and other layers suitably selected as needed is laminated. The thickness of the filter layer is not specifically limited and may be, for example, about 0.5 to 20 micrometers.

The filter layer may be laminated by direct application on the substrate or the like with the recording layer, or may be laminated on a base material such as a film to prepare a filter layer which is then laminated on the substrate.

First Gap Layer

The first gap layer is formed as needed between the filter layer and the reflective film to flatten the surface of the lower substrate. It is also effective for adjusting the size of the hologram that is formed in the recording layer. That is, since the recording layer should form a certain size of the interference region of the recording-use reference light and the informing light, it is effective to provide a gap between the recording layer and the servo pit pattern.

For example, the first gap layer can be formed by applying a material such as an ultraviolet radiation-curing resin from above the servo pit pattern and curing it. When employing a filter layer formed by application on a transparent base material, the transparent base material can serve as the first gap layer.

The thickness of the first gap layer is not specifically limited, and can be suitably selected based on the objective. A thickness of 1 to 200 micrometers is desirable.

Second Gap Layer

The second gap layer is provided as needed between the recording layer and the filter layer.

The material of the second gap layer is not specifically limited, and may be suitably selected based on the objective. Examples are: transparent resin films such as triacetyl cellulose (TAC), polycarbonate (PC), polyethylene terephthalate (PET), polystyrene (PS), polysulfone (PSF), polyvinylalcohol (PVA), and poly(methyl methacrylate) (PMMA); and norbornene resin films such as a product called ARTON film made by JSR Corporation and a product called Zeonoa made by Japan Zeon Co. Of these, those that are highly isotropic are desirable, with TAC, PC, the product called ARTON, and the product called Zeonoa being preferred.

The thickness of the second gap layer is not specifically limited and may be suitably selected based on the objective. A thickness of 1 to 200 micrometers is desirable.

Specific embodiments of the holographic recording medium of the present invention will be described in greater detail below. However, the present invention is not limited to these specific embodiments.

First Implementation Embodiment

FIG. 1 is a schematic cross-sectional view of the configuration of the holographic recording medium according to the first implementation embodiment. In holographic recording medium 21 according to the first implementation embodiment, a servo pit pattern 3 is formed on substrate 1 made of polycarbonate resin or glass, and aluminum, gold, platinum, or the like is coated on servo pit pattern 3 to provide reflective film 2. In FIG. 1, servo pit pattern 3 has been formed over the entire surface of lower substrate 1, but the servo pit pattern may be formed cyclically. Servo pit pattern 3 is normally 1,750 Angstroms (175 nm) in height, and is quite small relative to the thickness of the substrate and the other layers.

First gap layer 8 is formed by spin coating or the like a material such as an ultraviolet radiation-curing resin on reflective film 2 of lower substrate 1. First gap layer 8 is effective for both the protection of reflective layer 2 and the adjustment of the size of the hologram formed in recording layer 4. That is, providing a gap between recording layer 4 and servo pit pattern 3 is effective for the formation of an interference area for the recording-use reference light and informing light of a certain size in recording layer 4.

Filter layer 6 is provided on first gap layer 8. Recording layer 4 is sandwiched between filter layer 6 and upper substrate 5 (a polycarbonate resin substrate or glass substrate) to form holographic recording medium 21.

FIG. 1 shows a filter layer 6 that passes only infrared radiation and blocks light of all other colors. Accordingly, since the informing light and recording and reproducing-use reference light are blue, they are blocked by filter layer 6 and do not reach reflective film 2. They return, exiting from entry and exit surface A.

Filter layer 6 is a multilayered vapor deposition film comprised of high refractive index layers and low refractive index layers deposited in alternating fashion.

Filter layer 6, comprised of a multilayered vapor deposition film, may be formed directly on first gap layer 8 by vacuum vapor deposition, or a film comprised of a multilayered vapor deposition film formed on a base material may be punched into the shape of a holographic recording medium to employed as filter layer 6.

In this embodiment, holographic recording medium 21 may be disk-shaped or card-shaped. When card-shaped, the servo pit pattern may be absent. In holographic recording medium 21, the lower substrate is 0.6 mm, first gap layer 8 is 100 micrometers, filter layer 6 is 2 to 3 micrometers, recording layer 4 is 0.6 mm, and upper substrate 5 is 0.6 mm in thickness, for a total thickness of about 1.9 mm.

Figure 3:
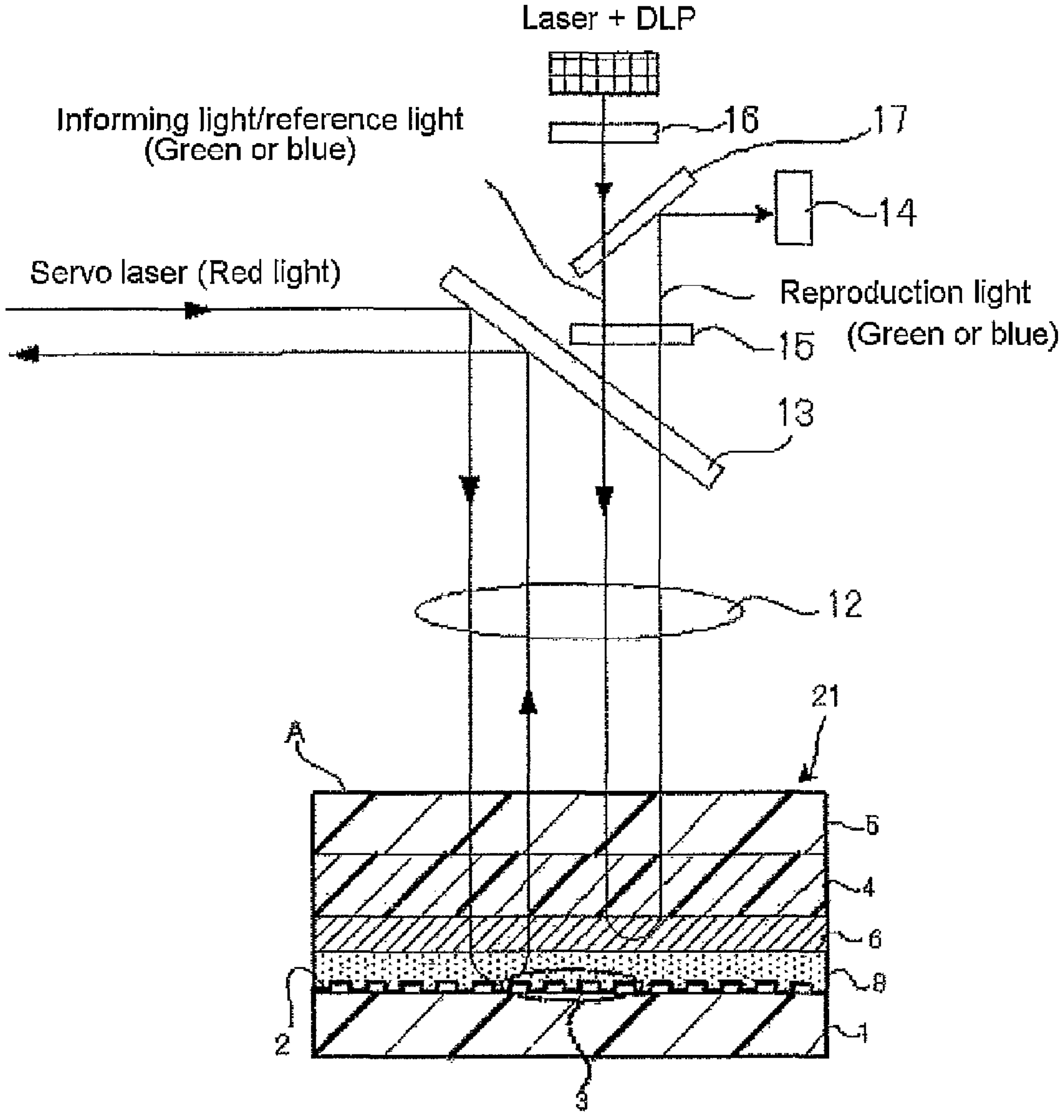
FIG. 3 is a drawing descriptive of an example of an optical system permitting recording and reproducing of information on a holographic recording medium.

An optical system applicable for the recording of information on and the reproduction of information from holographic recording medium 21 will be described with reference to FIG. 3.

First, a light (red light) emitted by a servo laser is nearly 100 percent reflected by dichroic mirror 13, passing through objective lens 12. Objective lens 12 directs the servo light onto holographic recording medium 21 so that it focuses at a point on reflective film 2. That is, dichroic mirror 13 passes light of green and blue wavelengths while reflecting nearly 100 percent of red light. The servo light entering entry and exit surface A to which and from which the light enters and exits of holographic recording medium 21 passes through upper substrate 5, recording layer 4, filter layer 6, and first gap layer 8, is reflected by reflective layer 2, and passes back through first gap layer 8, filter layer 6, recording layer 4, and upper substrate 5, exiting entry and exit surface A. The returning light that exits passes through objective lens 12, is nearly 100 percent reflected by dichroic mirror 13, and the servo information is detected by a servo information detector (not shown in FIG. 3). The servo information that is detected is employed for focus servo, tracking servo, slide servo, and the like. When the hologram material (the polymerizable compound of the present invention) included in recording layer 4 is not sensitive to red light, the servo light passes through recording layer 4 without affecting recording layer 4, even when the servo light is randomly reflected by reflective film 2. Since the light in the form of the servo light reflected by reflective film 2 is nearly 100 percent reflected by dichroic mirror 13, the servo light is not detected by a CMOS sensor or CCD 14 for reproduction image detection and thus does not constitute noise to the reproduction light.

The informing light and recording-use reference light generated by the recording/reproducing laser passes through polarizing plate 16 and is linearly polarized. It then passes through half mirror 17, becoming circularly polarized light at the point where it passes through ¼ wavelength plate 15. The light then passes through dichroic mirror 13, and is directed by objective lens 12 onto holographic recording medium 21 so that the informing light and recording-use reference light form an interference pattern in recording layer 4. The informing light and recording-use reference light enter through entry and exit surface A, interfering with each other to form an interference pattern in recording layer 4. Subsequently, the informing light and recording-use reference light pass through recording layer 4, entering filter layer 6. However, they are reflected before reaching the bottom surface of filter layer 6, returning. That is, neither the informing light nor the recording-use reference light reaches reflective film 2. That is because filter layer 6 is a multilayered vapor deposition layer in which multiple high refractive index and low refractive index layers are alternatively laminated, and has the property of passing only red light.

Second Implementation Embodiment

Figure 2:
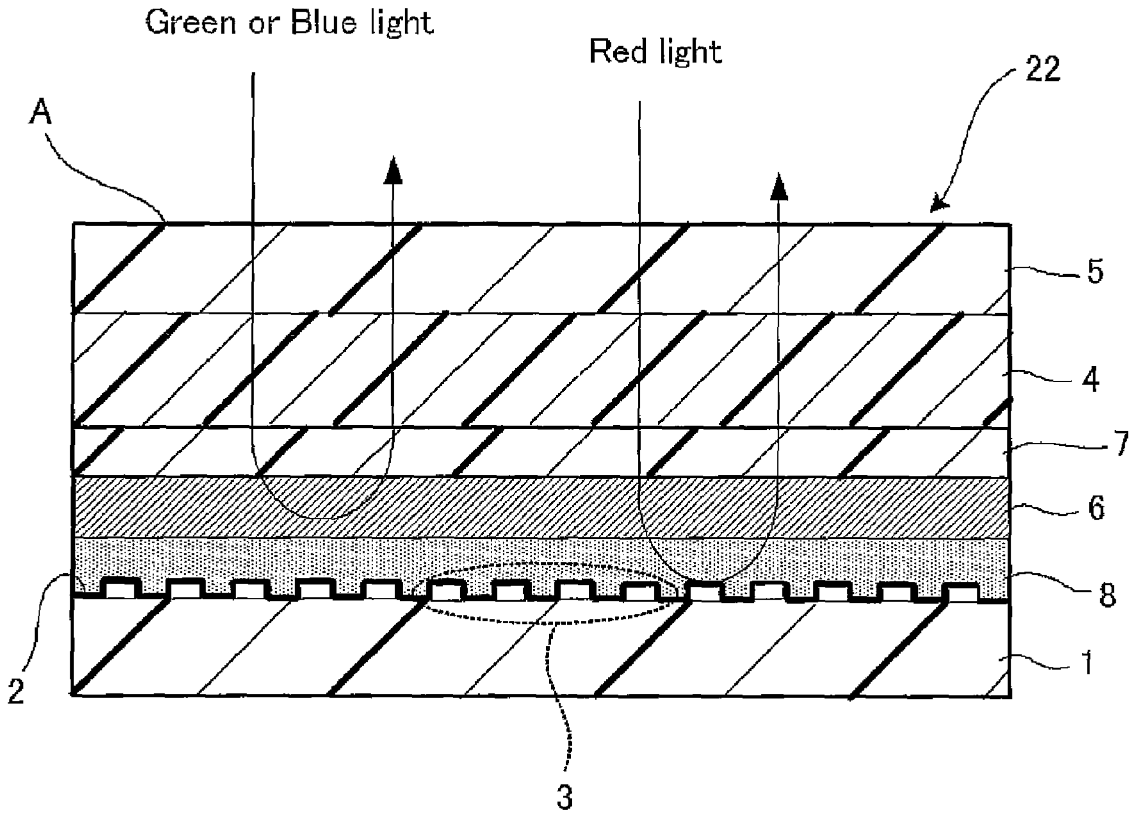
FIG. 2 is a schematic cross-sectional view of an example of a holographic recording medium according to a second implementation embodiment.

FIG. 2 is a schematic cross-sectional view of the configuration of the holographic recording medium according to the second implementation embodiment. A servo pit pattern 3 is formed on substrate 1 made of polycarbonate resin or glass in the holographic recording medium 22 according to the second implementation embodiment. Reflective film 2 is provided by coating aluminum, gold, platinum, or the like on the surface of servo pit pattern 3. Servo pit pattern 3 is normally 1,750 Angstroms (175 nm) in height in the same manner as in the first implementation embodiment.

The configuration of the second implementation embodiment differs from that of the first implementation embodiment in that second gap layer 7 is provided between filter layer 6 and recording layer 4 in holographic recording medium 22 according to the second implementation embodiment. A point at which the informing light and reproduction light are focused is present in second gap layer 7. When this area is embedded in a photopolymer, excessive consumption of monomer occurs due to excess exposure, and multiplexing recording capability diminishes. Accordingly, it is effective to provide a nonreactive transparent second gap layer.

Filter layer 6 in the form of a multilayered vapor deposition film comprised of multiple layers in which multiple high refractive index and low refractive index layers are alternately laminated is formed over first gap layer 8 once first gap layer 8 has been formed, and the same one as employed in the first implementation embodiment can be employed as filter layer 6 in the second implementation embodiment.

In holographic recording medium 22 of the second implementation embodiment, lower substrate 1 is 1.0 mm, first gap 8 is 100 micrometers, filter layer 6 is 3 to 5 micrometers, second gap layer 7 is 70 micrometers, recording layer 4 is 0.6 mm, and upper substrate 5 is 0.4 mm in thickness, for a total thickness of about 2.2 mm.

When recording or reproducing information, a red servo light and a green informing light and recording/reproducing reference light are directed onto holographic recording medium 22 of the second implementation embodiment having the configuration set forth above. The servo light enters through entry and exit surface A, passing through recording layer 4, second gap layer 7, filter layer 6, and first gap layer 8, and is reflected by reflective film 2, returning. The returning light then passes sequentially back through first gap layer 8, filter layer 6, second gap layer 7, recording layer 4, and upper substrate 5, exiting through entry and exit surface A. The returning light that exits is used for focus servo, tracking servo, and the like. When the hologram material included in recording layer 4 (the polymerizable compound of the present invention) is not sensitive to red light, the servo light passes through recording layer 4 and is randomly reflected by reflective film 2 without affecting recording layer 4. The green informing light and the like enters through entry and exit surface A, passing through recording layer 4 and second gap layer 7, and is reflected by filter layer 6, returning. The returning light then passes sequentially back through second gap layer 7, recording layer 4, and upper substrate 5, exiting through entry and exit layer A. During reproduction, as well, the reproduction-use reference light and the reproduction light generated by irradiating the reproduction-use reference light onto recording layer 4 exit through entry and exit surface A without reaching reflective film 2. The optical action around holographic recording medium 22 (objective lens 12, filter layer 6, and detectors in the form of CMOS sensors or CCD 14 in FIG. 3) is identical to that in the first implementation embodiment and thus the description thereof is omitted.

Information Recording Method

The present invention also relates to a method of recording information on the holographic recording medium of the present invention. The information recoding method of the present invention comprises forming an interference image on the recording layer comprised in the holographic recording medium by irradiation of an informing light and a reference light to the recording layer, and irradiating a fixing light to the recording layer on which the interference image has been formed to fix the interference image. When an informing light with a wavelength of equal to or greater than 400 nm and a fixing light with a wavelength of less than 400 nm are employed, it is possible to compensate for the volumetric shrinkage produced by irradiation of the informing light by modulating the refractive index through irradiation of the fixing light, as set forth above.

A light having coherent properties can be employed as the informing light. By irradiating the informing light and reference light onto the recording medium so that the optical axes of the informing light and reference light are coaxial, it is possible to record in the recording layer an interference image generated by interference of the informing light and reference light. Specifically, a informing light imparted with a two dimensional intensity distribution and a reference light of intensity nearly identical to that of the informing light are superposed in the recording layer and the interference pattern that they form is used to generate an optical characteristic distribution in the recording layer, thereby recording information. The wavelengths of the informing light and reference light are preferably equal to or greater than 400 nm, more preferably 400 to 2,000 mm, and further preferably, 400 to 700 nm.

After recording information (forming an interference image) by irradiating the informing light and reference light, a fixing light is irradiated to fix the interference image. As set forth above, the wavelength of the fixing light is preferably less than 400 nm, more preferably equal to or greater than 100 nm but less than 400 nm, and further preferably, equal to or greater than 200 nm but less than 400 nm.

Information can be reproduced by irradiating a reference light onto an interference image formed by the above-described method. In the course of reading (reproducing) information that has been written, just a reference light is irradiated onto the recording layer with the same arrangement as during recording, causing a reproduction light having an intensity distribution corresponding to the optical characteristic distribution formed in the recording layer to exit the recording layer.

An optical recording and reproducing device suited to use in the recording and reproducing of information in the holographic recording medium of the present invention will be described with reference to FIG. 4.

Figure 4:
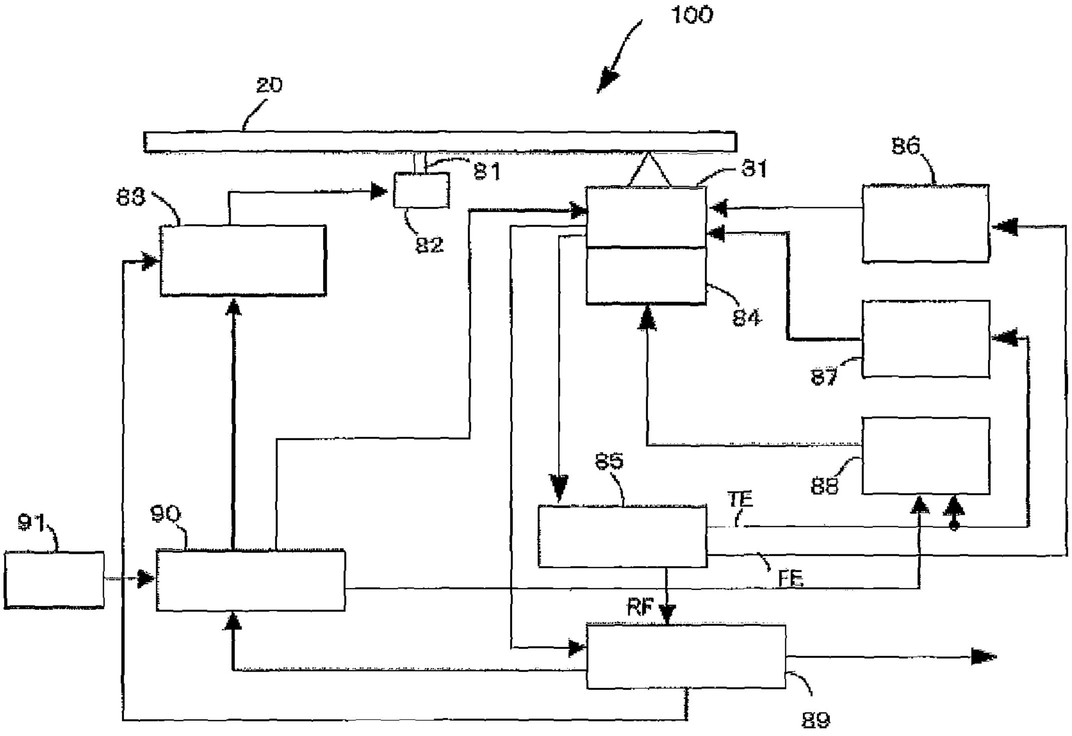
FIG. 4 is a block diagram showing an example of the overall configuration of a recording and reproducing device suited to use in recording and reproducing information on the holographic recording medium of the present invention.

The optical recording and reproducing device 100 of FIG. 4 is equipped with spindle 81 on which is mounted holographic recording medium 20, spindle motor 82 rotating spindle 81, and spindle servo circuit 83 controlling spindle motor 82 so that it maintains holographic recording medium 20 at a prescribed rpm level.

Recording and reproducing device 100 is further equipped with pickup 31 for recording information by irradiating a informing light and a recording-use reference light onto holographic recording medium 20, and for reproducing information that has been recorded on holographic recording medium 20 by irradiating a reproducing-use reference light onto holographic recording medium 20 and detecting the reproduction light; and driving device 84 capable of moving pickup 31 radially with respect to holographic recording medium 20.

Optical recording and reproducing device 100 is equipped with detection circuit 85 for detecting focus error signal FE, tracking error signal TE, and reproduction signal RF based on the output signals of pickup 31; focus servo circuit 86 that operates a focus servo by driving an actuator in pickup 31 to move an objective lens (not shown in FIG. 4) in the direction of thickness of holographic recording medium 20 based on focus error signal FE detected by detection circuit 85; tracking servo circuit 87 that operates a tracking servo by driving an actuator in pickup 31 to move an objective lens in the radial direction of holographic recording medium 20 based on tracking error signal TE detected by detection circuit 85; and slide servo circuit 88 that operates a slide servo by controlling drive device 84 to move pickup 31 in the radial direction of holographic recording medium 20 based on instructions from a controller, described further below, and tracking error signal TE.

Optical recording and reproducing device 100 is further equipped with signal processing circuit 89 that decodes the output data of a CCD array or CMOS in pickup 31 to reproduce data recorded in the data areas of holographic recording medium 20, reproduces a base clock based on reproduction signal RF from detection circuit 85, and determines addresses; controller 90 that effects overall control of optical recording and reproducing device 100; and operation element 91 providing various instructions to controller 90. Controller 90 inputs the base clock and address information outputted by signal processing circuit 89 and controls pickup 31, spindle servo circuit 83, slide servo circuit 88, and the like. Spindle servo circuit 83 inputs the base clock that is outputted by signal processing circuit 89. Controller 90 comprises a central processing unit (CPU), read only memory (ROM), and random access memory (RAM). The functions of controller 90 can be realized by having the CPU that employs the RAM as a work area and execute programs stored in the ROM.

EXAMPLES

The present invention will be described in detail below based on examples. However, the present invention is not limited to the examples.

Example 1

Synthesis of Example Compound RR-1

Example compound RR-1 was synthesized according to the following scheme.

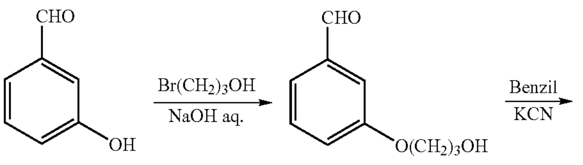

Synthesis Intermediate 1

-continued

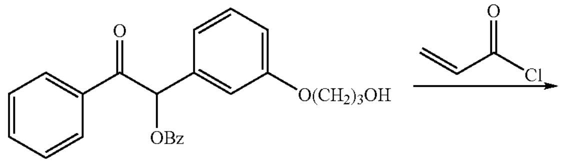

Synthesis Intermediate 2

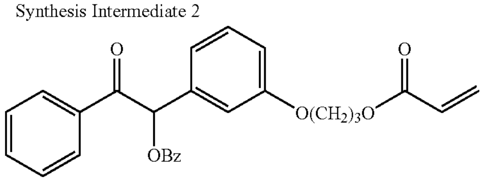

Example Compound RR-1

(Synthesis of Synthesis Intermediate 1)

A 36 g quantity of sodium hydroxide was dissolved in 1.5 L of water and 105.4 g of 3-hydroxybenzaldehyde was added. To this solution was added dropwise 100 g of 3-bromopropanol and the mixture was heated to reflux (for 6 hours). The mixture was cooled to room temperature and 5 g of sodium hydroxide and 1 L of ethyl acetate were added to separate the solution. The organic layer was washed with 200 mL of diluted hydrochloric acid, washed with saturated sodium chloride aqueous solution, and dried by adding magnesium sulfate. The solid component was filtered out and the solvent was distilled off under reduced pressure. The residue was purified by silica gel chromatography, yielding 100 g of synthesis intermediate 1.

(Synthesis of Synthesis Intermediate 2)

A 4.29 g quantity of benzyl and 13.67 g of synthesis intermediate 1 were dissolved in 15 mL of dimethyl sulfamide. The solution was cooled with ice and 0.26 g of potassium cyanide was added. The mixture was stirred for one hour at room temperature, after which 100 mL of ethyl acetate and 50 mL of saturated sodium hydrogencarbonate aqueous solution were added to separate the solution. The organic layer was washed with 50 mL of saturated sodium chloride aqueous solution and dried by adding magnesium sulfate. The solid component was filtered out and the solvent was distilled off under reduced pressure. The residue was purified by silica gel chromatography, yielding 4.4 g of synthesis intermediate 2.

(Synthesis of Example Compound RR-1)

A 2.8 g quantity of synthesis intermediate 2 was dissolved in 20 mL of ethyl acetate, the solution was cooled with ice, and 1.5 mL of triethylamine and 0.05 g of hydroquinone were added. To this solution was added dropwise 0.9 mL of acrylic acid chloride. The mixture was stirred for one hour at room temperature, and 100 mL of ethyl acetate and 50 mL of diluted hydrochloric acid were added to separate the solution. The organic layer was washed with saturated sodium chloride aqueous solution and dried by adding magnesium sulfate. The solid component was filtered out and the solvent was distilled off under reduced pressure. The residue was purified by silica gel chromatography, yielding 1.0 g of Example Compound RR-1. The identification results of the compound thus obtained are given below.

$^1H$ NMR (300 MHz, $CDCl_3$) δ 2.17(m, 2H) 4.06(m, 3 H) 4.35 (m, 2H) 5.81(d, 1H) 6.12(dd, 1H) 6.41(d, 1H) 6.9~7.6 (m, 11H) 8.01(d, 1H) 8.13(d, 2H)

Example 2

Preparation of Holographic Recording Composition

A 31.5 g quantity of biscyclohexylmethane diisocyanate, 61.2 g of polypropyleneoxidetriol (weight average molecular weight of 1,000), 2.5 g of tetramethylene glycol, 3.1 g of monomer (M-1) of the structural formula given below, 0.39 g of photopolymerization initiator (TPO-L, made by BASF Corp.), 1.01 g of dibutyl dilaurate, and 0.3 g of Example Compound RR-1 were admixed under a nitrogen flow to prepare a holographic recording composition.

M-1

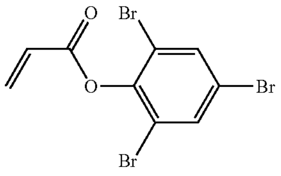

Comparative Example 1

Preparation of Holographic Recording Composition

A 31.5 g quantity of biscyclohexylmethane diisocyanate, 61.2 g of polypropyleneoxidetriol (weight average molecular weight of 1,000), 2.5 g of tetramethylene glycol, 3.1 g of monomer (M-1), 0.39 g of photopolymerization initiator (TPO-L, made by BASF Corp.), and 1.01 g of dibutyl dilaurate were admixed under a nitrogen flow to prepare a holographic recording composition.

Example 3 and Comparative Example 2

Preparation of Holographic Recording Medium

A first substrate was prepared by subjecting one side of a glass sheet 0.5 mm in thickness to an antireflective treatment to impart a reflectance of 0.1 percent for perpendicularly incident light with the wavelength of the recording light.

A second substrate was prepared by subjecting one side of a glass sheet 0.5 mm in thickness to an aluminum vapor deposition treatment to impart a reflectance of 90 percent for perpendicularly incident light with the wavelength of the recording light.

A transparent polyethylene terephthalate sheet 500 micrometers in thickness was provided as a spacer on the side of the first substrate that had not been subjected to the antireflective treatment.

The holographic recording compositions of Example 2 and Comparative Example 1 were each separately placed on first substrates, the aluminum vapor deposited surface of the second substrates were stacked on the holographic recording composition in such a manner that air was not entrained, and the first and second substrates were bonded through the spacer. The holographic recording layer formed was 500 micrometers in thickness. The holographic recording layer was left standing for 24 hours at 45° C. to prepare the holographic recording media of Example 3 and Comparative Example 2.

<Recording in the Holographic Recording Medium and Evaluation>

Employing a collinear hologram recording and reproducing tester (B-VRD, made by Pulsetec Industrial Co., Ltd.), a series of multiplexed holograms was written into the holographic recording media of Example 3 and Comparative Example 2 and the sensitivity (recording energy) and level of multiplexing were measured and evaluated.

—Sensitivity Measurement—

The beam energy during recording ($mJ/cm^2$) was varied and the change in error rate of the reproduced signal (BER: bit error rate) was measured. Normally, there is such a tendency that the luminance of the reproduced signal increases and the BER of the reproduced signal gradually drops with an increase in the irradiated light energy. In the measurement, the lowest light energy at which a fairly good reproduced image (BER $<10^{-3}$) was obtained was adopted as the recording sensitivity of the holographic recording medium.

—Volumetric Shrinkage of Medium—

Figure 5:
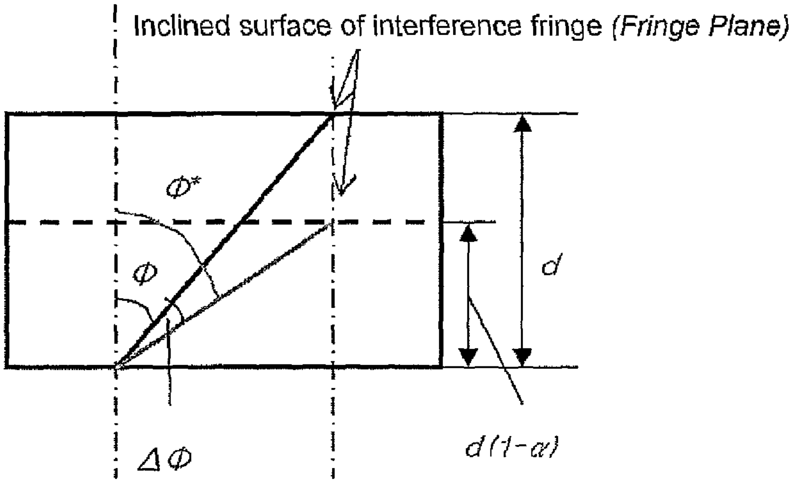
FIG. 5 shows a conceptual diagram of an FPR model.

Calculation from changes in the interference fringe due to planar wave two-beam interference is a known means of analyzing photopolymer shrinkage and expansion. In the fringe plane rotation (FPR) model, it is possible to evaluate shrinkage of the recording layer occurring between recording and reproduction from the difference between the angle during recording of a Bragg grating recorded at an angle on a recording medium and the optimal reproduction angle following recording (or after fixing). FIG. 5 is a conceptual diagram of this model. It is supposed that change in shrinkage before and after recording occurs in just the direction of thickness.

The change in incline of the interference fringe in the FPR model is given by the following equation.

$$\Phi^*=\Phi+\Delta\Phi=\arctan[\tan\Phi/(1-\alpha)]$$

In the above equation, $\Phi$ denotes the incline of the interference fringe during recording and $\Phi^*$ denotes the incline of the interference fringe during reproduction, and $\alpha$ denotes the rate of change in the recording layer.

A planar wave two-beam interference device with a 405 mm laser was used to record an interference fringe with a prescribed angle $\Phi$ at a weak diffraction efficiency (equal to or less than 1 percent) on a recording medium. Subsequently, a fixing light with a wavelength of 365 nm was irradiated onto the recording medium. When the photoreactive component of the recording medium had been completely consumed, the dependence of diffraction efficiency on the reproduction angle was measured and the angle of the interference fringe was measured again. The shrinkage rate $\alpha$ of the recording medium was estimated using the above equation with the change in the angle of incline of the interference fringe during recording and following the fixation operation. The results showed that the holographic recording medium of Example 3 employing the holographic recording composition of Example 2 underwent less volumetric shrinkage than the holographic recording medium of Comparative Example 2 employing the holographic recording composition of Comparative Example 1.

The optical recording composition of the present invention can provide a holographic recording medium capable of recording and reproducing with high precision by compensating for volumetric shrinkage. The polymerizable compound and optical recording composition of the present invention are suitable recording materials for various volume hologram-type optical recording media capable of high-density image recording.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

What is claimed is:

1. A polymerizable compound denoted by general formula (1):

General formula (1)

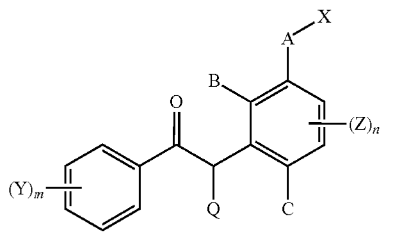

wherein A denotes an oxygen atom, sulfur atom, or NR, R denotes a hydrogen atom, alkyl group, aryl group, or heterocyclic group, Y and Z each independently denote a halogen atom, polymerizable group, optionally polymerizable group-substituted alkyl group, aryl group, heterocyclic group, cyano group, nitro group, hydroxy group, amino group, carboxy group, acyl group, alkoxy group, aryloxy group, acyloxy group, acylamino group, sulfonamide group, alkoxycarbonyl group, aryloxycarbonyl group, carbamoyl group, or sulfamoyl group, B and C each independently denote a hydrogen atom, halogen atom, polymerizable group, optionally polymerizable group-substituted alkyl group, aryl group, heterocyclic group, cyano group, nitro group, hydroxy group, amino group, carboxy group, acyl group, alkoxy group, aryloxy group, acyloxy group, acylamino group, sulfonamide group, alkoxycarbonyl group, aryloxycarbonyl group, carbamoyl group, or sulfamoyl group, wherein at least one from among B and C denotes a hydrogen atom and at least one from among X, Y, and Z comprises a polymerizable group, m denotes an integer ranging from 0 to 5 and plural Ys may be identical or different from each other when m is an integer of equal to or greater than 2, n denotes an integer ranging from 0 to 2 and plural Zs may be identical or different from each other when n is 2, and Q denotes an elimination group, and X is a group represented by general formula (2):

-L-G General formula (2)

wherein L represents a divalent linking group comprised of a combination of an alkylene group or arylene group with at least one selected from the group consisting of —O—, —S—, —C(═O)—, —$SO_2$—, —$NR^1$—, an alkylene group, and an arylene group, $R^1$ denotes a hydrogen atom or a substituent, and G is selected from the group consisting of:

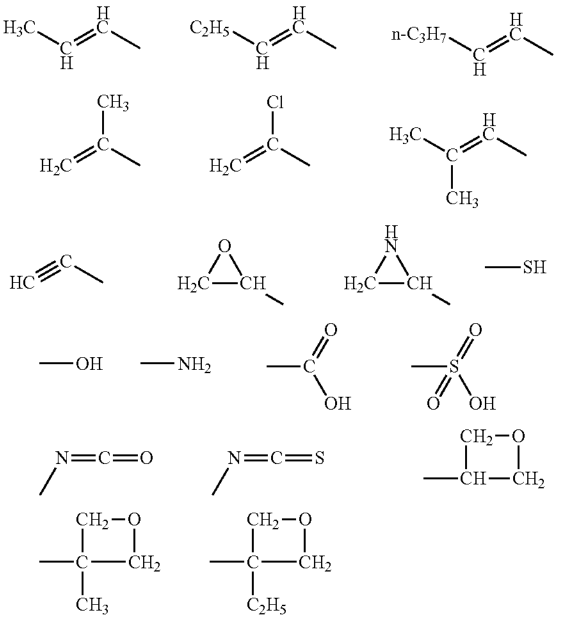

(M-1)

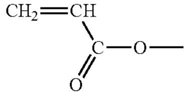

-continued (M-2)

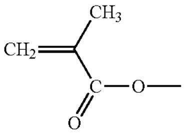

(M-3)

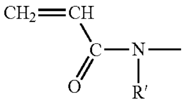

(M-4)

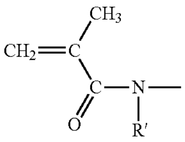

(M-5)

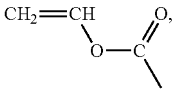

and (M-6)

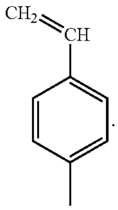

2. The polymerizable compound of claim 1, wherein A in general formula (1) denotes an oxygen atom.

3. The polymerizable compound of claim 1, wherein Q in general formula (1) is an elimination group denoted by general formula (3):

General formula (3)

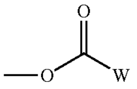

wherein W denotes an alkyl group, aryl group, or heterocyclic group.

4. A holographic recording medium comprising a recording layer, wherein the recording layer comprises the polymerizable compound of claim 1.

5. A method of recording information on the holographic recording medium of claim 4 comprising:

forming an interference image on the recording layer comprised in the holographic recording medium by irradiation of an informing light and a reference light to the recording layer, and irradiating a fixing light to the recording layer on which the interference image has been formed to fix the interference image.

6. The method of recording information of claim 5, wherein the informing light has a wavelength of equal to or greater than 400 nm and the fixing light has a wavelength of less than 400 nm.

7. The polymerizable compound of claim 1, wherein G is an acryloyloxy group.

* * * * *